(12) United States Patent
Shull

(10) Patent No.: US 7,517,891 B2
(45) Date of Patent: Apr. 14, 2009

(54) CAMPTOTHECIN DERIVATIVES AND IMPROVED SYNTHETIC METHODS

(75) Inventor: Brian Keith Shull, Durham, NC (US)

(73) Assignee: Glyconix Corporation, New York, NY (US)

( * ) Notice: Subject to any disclaimer, the term of this patent is extended or adjusted under 35 U.S.C. 154(b) by 159 days.

(21) Appl. No.: 11/588,021

(22) Filed: Oct. 26, 2006

(65) Prior Publication Data

US 2007/0099948 A1    May 3, 2007

Related U.S. Application Data

(60) Provisional application No. 60/730,566, filed on Oct. 27, 2005.

(51) Int. Cl.
*A61K 31/4745* (2006.01)
*C07D 491/14* (2006.01)

(52) U.S. Cl. .................. 514/283; 536/4.1; 536/17.2; 536/17.9; 536/18.1; 546/51

(58) Field of Classification Search ............... 514/283; 546/51; 536/4.1, 17.2, 17.9, 18.1
See application file for complete search history.

(56) References Cited

U.S. PATENT DOCUMENTS 5,677,286 A * 10/1997 Shull et al. ................ 514/25

* cited by examiner

*Primary Examiner*—Shaojia Anna Jiang
*Assistant Examiner*—Ganapathy Krishnan
(74) *Attorney, Agent, or Firm*—Medlen & Carroll, LLP

(57) ABSTRACT

The present invention relates to compositions and methods for preparing pharmaceutical compositions. In some embodiments, the invention includes compounds and methods of resolving chiral compounds. In some embodiments, the invention includes chiral and crystalline compositions and hydrates. In some embodiments, the invention contemplates compositions comprising camptothecin derivatives and synthetic intermediates thereof. In some embodiments, the invention includes methods of protecting, inserting, modifying, separating isomers, and removing chemical groups.

2 Claims, 11 Drawing Sheets

HAR-7 purified alpha-linked isomer

CAMPTOTHECIN DERIVATIVES AND IMPROVED SYNTHETIC METHODS

This application for patent under 35 U.S.C. § 111(a) claims priority to Provisional Application(s) Ser. No. 60/730,566 filed on Oct. 27, 2005 under 35 U.S.C. § 111(b).

FIELD OF THE INVENTION

The present invention relates to compositions and methods for preparing pharmaceutical compositions. In some embodiments, the invention includes compounds and methods of resolving chiral compounds. In some embodiments, the invention includes chiral and crystalline compositions and hydrates. In some embodiments, the invention contemplates compositions comprising camptothecin derivatives and synthetic intermediates thereof. In some embodiments, the invention includes methods of protecting, inserting, modifying, separating isomers, and removing chemical groups.

BACKGROUND OF THE INVENTION

One enantiomeric or diastereomeric isomer of a compound can possessed differing pharmacological activity than another. Pharmaceuticals compositions that contain compounds with multiple isomers increase the chances of undesired and adverse drug reactions. Regulatory agencies (e.g. FDA) throughout the world are currently reviewing the importance of diastereomeric and enantiomeric purity with regard to pharmaceutical and agrochemical products. New guidelines from such agencies have been key drivers for the focus on single isomeric products in these industries. Thus, there is a need to identify time and cost efficient methods of producing synthetically valuable compositions that result in single chiral compound compositions and methods for facilitating the separation and resolution chiral compounds.

Numerous chemical agents have been devised for the treatment of cancer with varying degrees of efficacy. However, no single drug has one hundred percent effectiveness against different cancers, and negative side-effects ranging from minor to serious are always present. On such compound that has received much attention due to its anticancer activity is camptothecin, a quinoline-based alkaloid found in the barks of the Chinese Camptotheca tree and the Asian nothapodytes tree. Camptothecin is also known by its chemical name 4(S)-ethyl-4-hydroxy-1H-pyrano-[3',4':6,7]indolizino[1,2-b]quinoline-3,14(4H,12H)-dione.

It is well-known that camptothecin including and derivatives are useful in treating breast cancers, ovarian cancer, colon cancer, malignant melanoma, small cell lung cancer, thyroid cancers, lymphomas, leukemias, and more recently AIDS; however, drug delivery is complicated by the fact that camptothecin is water-insoluble in its unmodified state. Several derivatives of camptothecin have been developed in order to address these problems including glycosylated derivatives. Shull et al., U.S. Pat. No. 5,677,286, Shull et al., U.S. Pat. No. 5,932,709, and Bouscarel et al., U.S. Pat. No. 6,407,117 and references cited therein are all hereby incorporated by reference. Several of these glycosylated derivatives are undergoing clinical evaluation. The methods disclosed to prepare these glycosylated derivatives result in compositions that are comprised of a mixture of enantiomers and/or diastereomers. To this end, there is a need to identify methods of preparing these compositions that provide improved isomeric purities of these camptothecin derivatives.

SUMMARY OF THE INVENTION

The present invention relates to compositions and methods for preparing pharmaceutical compositions. In some embodiments, the invention includes compounds and methods of resolving chiral compounds. In some embodiments, the invention includes chiral and crystalline compositions and hydrates. In some embodiments, the invention contemplates compositions comprising camptothecin derivatives and synthetic intermediates thereof. In some embodiments, the invention includes methods of protecting, inserting, modifying, separating isomers, and removing chemical groups.

In some embodiments, the invention relates to a method comprising i) mixing first camptothecin compound with a haloalkyl carboxylic acid under conditions such that a second camptothecin compound comprising a haloalkyl ester is produced; ii) mixing said second camptothecin compound with a chiral compound under conditions such that a first diastereomer and a second diastereomer are formed; iii) separating said first diastereomer and said second diastereomer under conditions such that an enriched composition is produced comprising said first diastereomer, wherein said first diastereomer is greater than 80% of the molecules comprising said first diastereomer and said second diastereomer in said enriched composition; and iii) mixing said diastereomerically enriched composition with ammonia or substituted ammonia under conditions such that a composition comprising a third camptothecin compound comprising an alcohol group is produced.

In some embodiments, the invention relates to a method comprising: i) mixing a first compound comprising a tertiary alcohol group with a halogenated alkyl carboxylic acid under conditions such that a second compound comprising an haloalkyl ester is produced; ii) mixing said second compound with a chemical reagent under conditions such that a third compound is produced comprising said haloalkyl ester, and iii) mixing said third compound with ammonia or substituted ammonia under conditions such that a composition comprising a fourth compound comprising a tertiary alcohol is produced.

In some embodiments, the invention relates to a method comprising: i) mixing a first compound comprising an alcohol group with a compound selected from the group consisting of 6-halohexanoic acid, substituted 6-halohexanoic acid, 5-halopentanonic acid, substituted 5-halopentanonic acid, 4-halobutyric acid, substituted 4-haloburyric acid, 3-halopropionic acid, substituted 3-halopropionic acid, 2-halobutyric acid, and substituted 2-halobutyric acid under conditions such that a haloalkyl ester is produced; ii) mixing said haloalkyl ester with a chiral compound under conditions such that a first diastereomer and a second diastereomer are formed; iii) separating said first diastereomer and said second diastereomer under conditions such that an enriched composition is produced comprising said first diastereomer and said second diastereomer, wherein said first diastereomer is greater than 80% of the molecules comprising said first diastereomer and said second diastereomer, and iii) mixing said enriched composition with ammonia or substituted ammonia under conditions such that a composition comprising a compound comprising an alcohol group is produced.

In some embodiments, the invention relates to a method comprising: i) mixing a first compound comprising an alcohol group with phosphorus pentoxide and a halogenated alkyl carboxylic acid under acidic conditions such that a haloalkyl ester is produced; ii) mixing said haloalkyl ester with a chiral compound under conditions such that a first diastereomer and a second diastereomer are formed; iii) separating said first diastereomer and said second diastereomer under conditions such that an enriched composition is produced comprising said first diastereomer and said second diastereomer, wherein said first diastereomer is greater than 80% of the molecules comprising said first diastereomer and said second diastereomer, and iii) mixing said enriched composition with ammonia or substituted ammonia under conditions such that a composition comprising a compound comprising a alcohol group is produced.

In some embodiments, the invention relates to the compound:

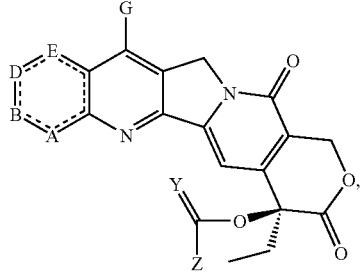

wherein, G is hydrogen or —[V(CH$_2$)$_p$W]$_q$-saccharide; V and W are the same or independently and individually sulfur, oxygen, nitrogen, or absent; p is 1 to 100; q is 0 to 100; --- is a double or single bond; A, B, D, and E are the same or different and independently C—R$^4$, oxygen, sulfur, nitrogen, or absent; Y is oxygen, nitrogen, or sulfur; Z is —(CR$^2$R$^3$)$_n$X; R$^2$, R$^3$, and R$^4$ are the same or different and independently hydrogen, halogen, hydroxy, oxo, cyano, nitro, amino, substituted amino, alkylamino, substituted alkylamine, dialkylamino, substituted dialkylamino, alkyl, substituted alkyl, alkoxy, substituted alkoxy, alkylthio, substituted alkylthio, haloalkyl, substituted haloalkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocycle alkyl, substituted heterocycle alkyl, —NR$_a$R$_b$, —NR$_a$C(=O)R$_b$, —NR$_a$ C(=O) NR$_a$NR$_b$, —NR$_a$C(=O)OR$_b$, —NR$_a$SO2R$_b$, —C(=O)R$_a$, C(=O)OR$_a$, —C(=O)NR$_a$R$_b$, —OC(=O)NR$_a$R$_b$, —OR$_a$, —SR$_a$, —SOR$_a$, —S(=O)$_2$R$_a$, —OS(=O)$_2$R$_a$ or —S(=O) 2OR$_a$; R$_a$ and R$_b$ is the same or different and independently hydrogen, alkyl, haloalkyl, substituted alkyl, aryl, substituted aryl, arylalkyl, substituted arylalkyl, heterocycle, substituted heterocycle, heterocycle alkyl or substituted heterocycle alkyl; n is 1 to 6, preferably 3 or 4; and X is a halogen.

In some embodiments, in some embodiments the invention relates to pharmaceutical formulations of the compounds which are administered to a subject for the treatment of cancers, breast cancers, ovarian cancer, colon cancer, malignant melanoma, small cell lung cancer, thyroid cancers, lymphomas, leukemias, and AIDS.

In some embodiments, the invention relates to the compound:

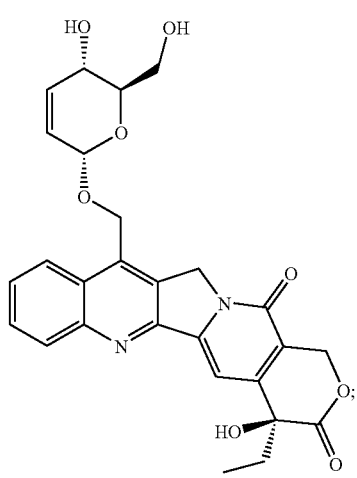

in substantially pure form. In further embodiments, the composition comprises a camptothecin saccharide compound of the following formula:

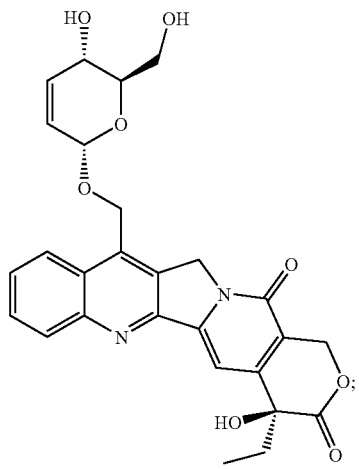

wherein said camptothecin saccharide compound is greater than 50%, 55%, 60%, 65%, 70%, 75%, 80%, 85%, 90%, 95%, 98%, 99%, 99.5% or 99.9% by weight of a camptothecin saccharide component.

In some embodiments, the compound is selected from the group consisting of:

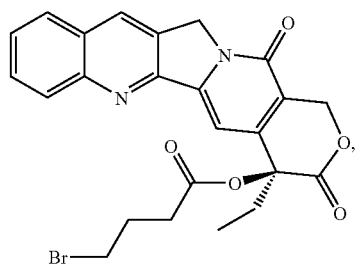

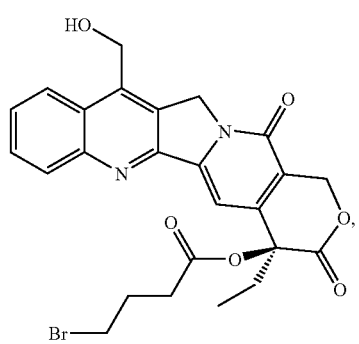

-continued

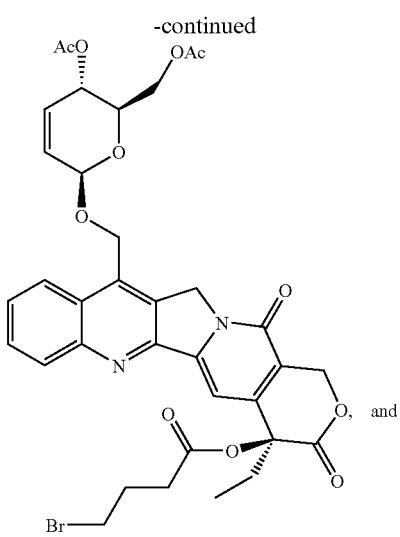

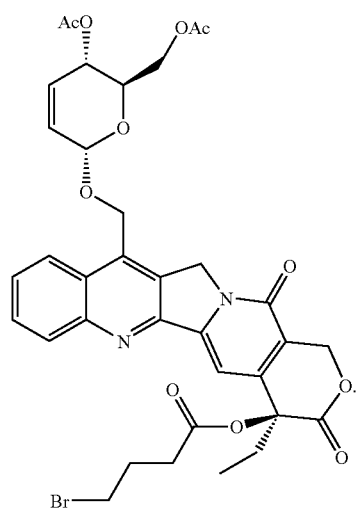

In some embodiments, the compound is:

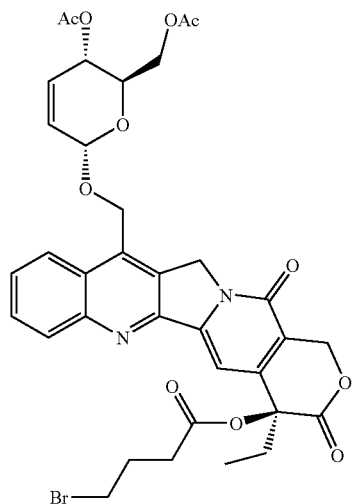

in substantially pure form.

In further embodiments, the composition comprises a camptothecin saccharide compound the following formula:

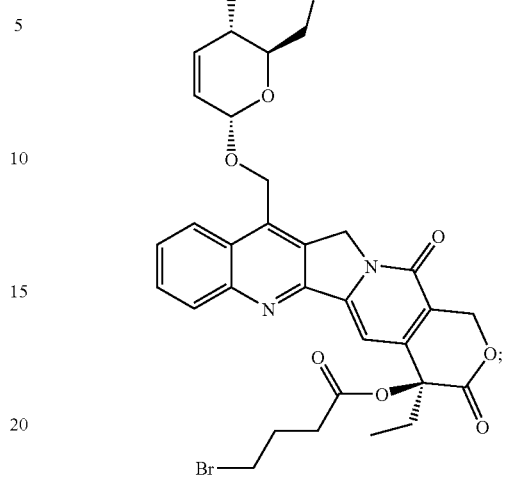

wherein said camptothecin saccharide compound is greater than 50%, 55%, 60%, 65%, 70%, 75%, 80%, 85%, 90%, 95%, 98%, 99%, 99.5% or 99.9% by weight of a camptothecin saccharide component.

In some embodiment, the invention relates to a method comprising mixing camptothecin with 4-bromobutyric acid, sulfuric acid, and phosphorus pentoxide under conditions such that a composition comprising a compound of the following formula:

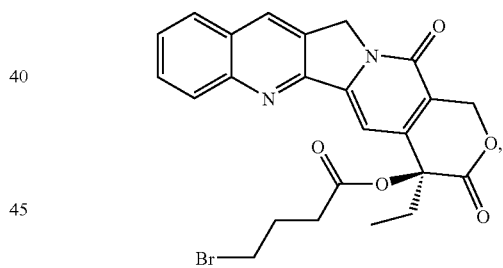

is produced. In further embodiments, the method comprises mixing a compound having the following formula:

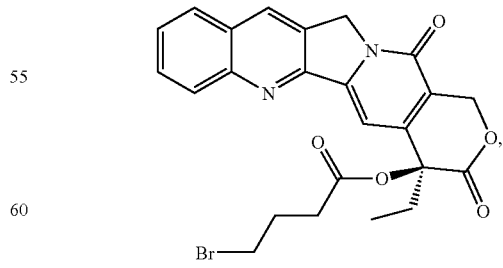

with ferrous sulfate and sulfuric acid under conditions such that a composition comprising a compound having the following formula:

is produced. In further embodiments, the method comprises mixing a compound having the following formula:

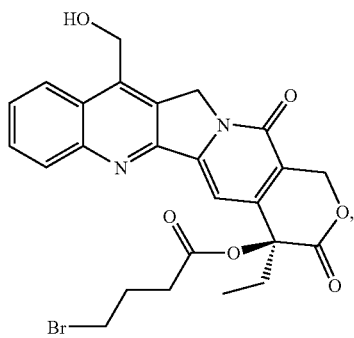

with tri-O-acetyl-D-glucal under conditions such that a composition comprising a compound having the following formula:

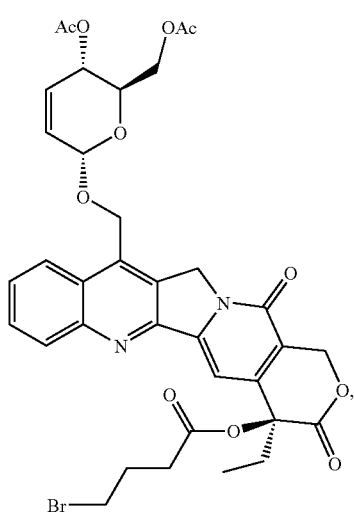

is produced. In further embodiments, the diastereomeric mixture of compounds at the aromatic center is purified by recrystallization in methanol. In further embodiments, the method comprises mixing a compound having the following formula:

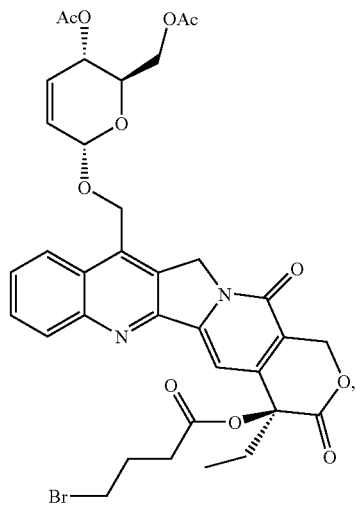

with ammonia under conditions such that a composition comprising a compound having the following formula:

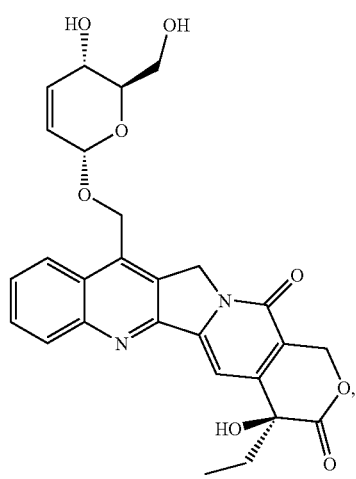

is produced.

In some embodiments, a compound is used for the manufacture of a medicament, wherein a) said compound has the following formula:

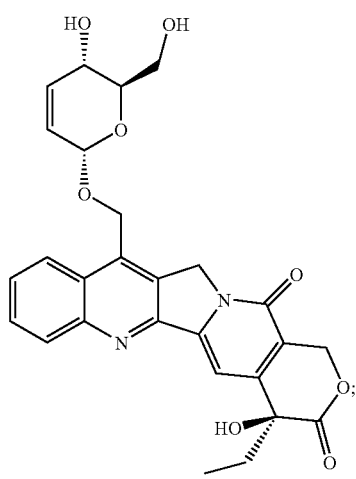

in a substantially pure form and b) said medicament is used to treat or prevent cancer.

In some embodiments the compound functioning to treat or prevent cancer is:

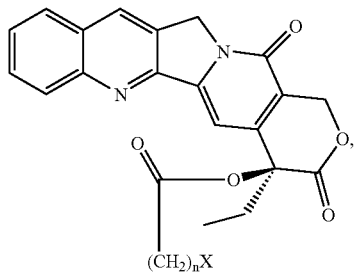

wherein n is 1 to 6, preferably 2, 3, or 4, and X is a halogen. In further embodiments, the compound functioning to prevent or treat cancer is the substituted or unsubstituted compound is:

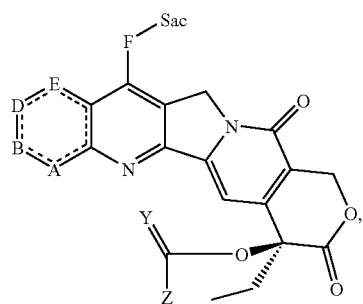

wherein, Sac is a substituted or unsubstituted saccharide; --- is a double or single bond; A, B, D, and E are the same or different and independently C—$R^4$, oxygen, sulfur, nitrogen, or absent; F is absent or a substituted or unsubstituted alkylene bridging group for example methylene (i.e., —$CH_2$—); Y is oxygen, sulfur or nitrogen, Z is —$(CR^2R^3)_nX$; $R^1$, $R^2$, $R^3$, and $R^4$ are the same or different and independently hydrogen, halogen, hydroxy, oxo, cyano, nitro, amino, substituted amino, alkylamino, substituted alkylamine, dialkylamino, substituted dialkylamino, alkyl, substituted alky, alkoxy, substituted alkoxy, alkylthio, substituted alkylthio, haloalkyl, substituted haloalkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocycle alkyl, substituted heterocycle alkyl, —$NR_aR_b$, —$NR_aC(\!=\!O)R_b$, —$NR_aC(\!=\!O)NR_aNR_b$, —$NR_aC(\!=\!O)OR_b$, —$NR_aSO_2R_b$, —$C(\!=\!O)R_a$, —$C(\!=\!O)OR_a$, —$C(\!=\!O)NR_aR_b$, —$OC(\!=\!O)NR_aR_b$, —$OR_a$, —$SR_a$, —$SORa$, —$S(\!=\!O)_2R_a$, —$OS(\!=\!O)_2R_a$ or —$S(\!=\!O)_2OR_a$; $R_a$ and $R_b$ is the same or different and independently hydrogen, alkyl, haloalkyl, substituted alkyl, aryl, substituted aryl, arylalkyl, substituted arylalkyl, heterocycle, substituted heterocycle, heterocycle alkyl or substituted heterocycle alkyl; n is 2-6; and X is a halogen, amino, substituted amino, alkylamino, substituted alkylamino, substituted hydroxy, alkoxy, substituted alkoxy, acyloxy, or substituted acyloxy.

In some embodiments, the invention relates to a method comprising: i) mixing a first compound comprising a tertiary alcohol group with sulfuric acid, phosphorus pentoxide and a compound selected from the group consisting of 4-halobutyric acid or 5-halopentanonic acid under conditions such halogenated alkyl ester is produced; ii) mixing said halogenated alkyl ester with a reagent under conditions such that a modified halogenated alkyl ester is produced, and iii) mixing said modified halogenated alkyl ester with ammonia or substituted ammonia under conditions such that a composition comprising second compound comprising a tertiary alcohol is produced. In further embodiments, the method comprises: i) mixing a first compound comprising an alcohol group with a compound selected from the group consisting of 4-halobutyric acid or 5-halopentanonic acid under conditions such halogenated alkyl ester is produced; ii) mixing said halogenated alkyl ester with a reagent under conditions such that a modified halogenated alkyl ester is produced, and iii) mixing said modified halogenated alkyl ester with ammonia or substituted ammonia under conditions such that a composition comprising second compound comprising said alcohol group is produced. In further embodiment, the method comprises: i) mixing a first compound comprising an alcohol group with a compound selected from the group consisting of 4-halobutyric acid, substituted 4-haloburyric acid, 5-halopentanonic, or substituted 5-halopentanonic acid under conditions such that a composition comprising a mixture of substituted or unsubstituted halogenated alkyl ester isomers is produced; ii) separating said isomers under conditions such that a composition comprising a separated halogenated alkyl ester isomer of greater than 80% purity by weight is produced, and iii) mixing said separated halogenated alkyl ester isomer with ammonia or substituted ammonia under conditions such that a composition comprising a compound comprising said alcohol group is produced.

In some embodiments, the invention relates to a compound selected from the group consisting of:

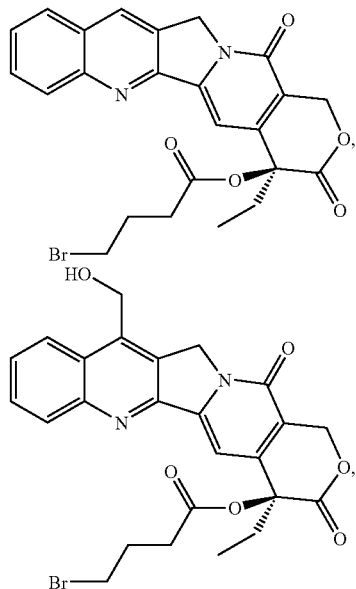

-continued
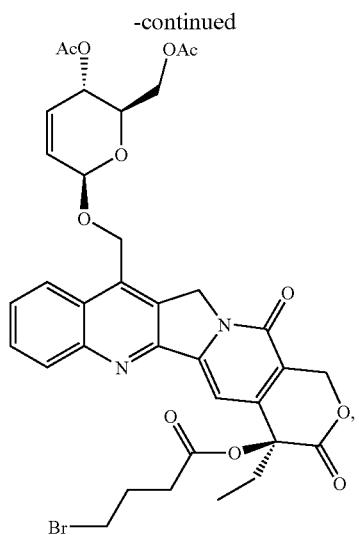
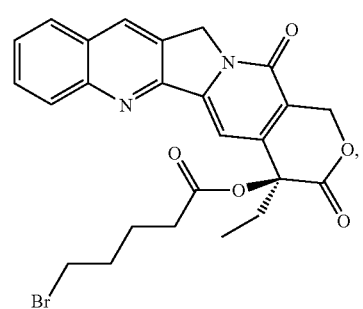
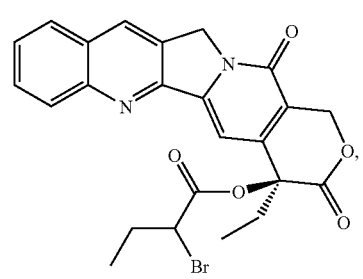
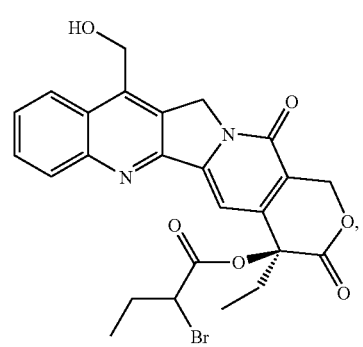
-continued
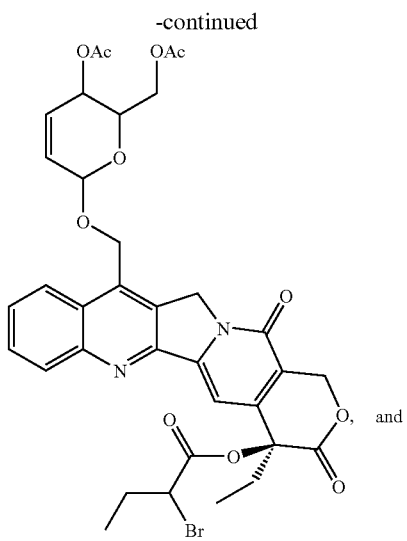
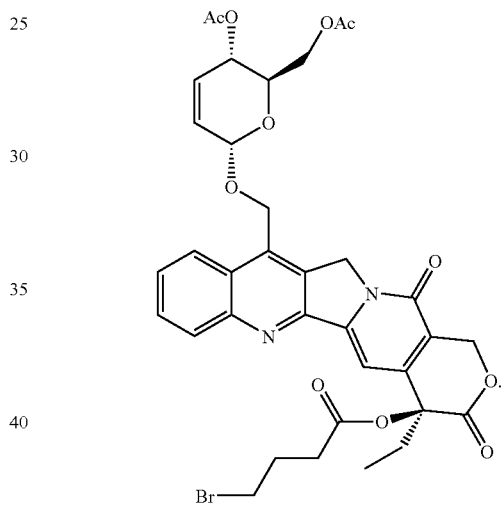
In some embodiments, the invention is a compound:
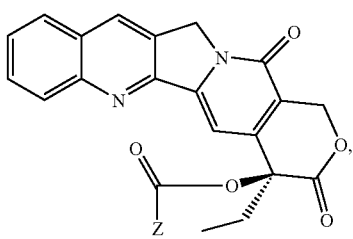
wherein, Z is —(CHR$^1$)$_n$X; R$^1$ is the same or different and independently hydrogen, halogen, or alkyl; n is 1 to 6; and X is hydrogen or halogen.

In some embodiments, the invention relates to a compound:

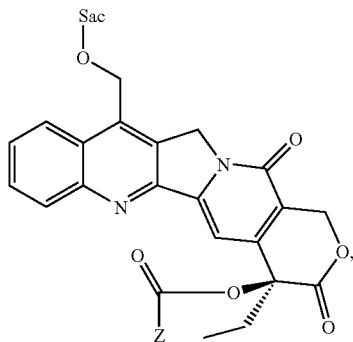

wherein, Sac is a saccharide or substituted saccharide; Z is —(CHR$^1$)$_n$X; R$^1$ is the same or different and independently hydrogen, halogen, or alkyl; n is 1 to 6; and X is hydrogen or halogen.

In some embodiments, the invention relates to a method comprising: forming a haloalkyl carboxylate ester with a tertiary alcohol and hydrolyzing said ester with ammonia. In further embodiments, the method comprises: forming a 2-halobutryate ester, 4-halobutyrate, or 5-halopentanoate ester with a tertiary alcohol and hydrolyzing said ester with ammonia.

In some embodiments, the invention relates to a method comprising: i) mixing a first compound comprising an alcohol group with a compound selected from the group consisting of 6-halohexanoic acid, substituted 6-halohexanoic acid, 5-halopentanonic acid, substituted 5-halopentanonic acid, 2-haloalkylcarboxylic acid, substituted 2-haloalkylcarboxylic acid, 4-halobutyric acid, substituted 4-haloburyric acid, 3-halopropionic acid, or substituted 3-halopropionic acid under conditions such that a halogenated alkyl ester is produced; ii) mixing said halogenated alkyl ester with a reagent under conditions such that a modified halogenated alkyl ester is produced, and iii) mixing said modified halogenated alkyl ester with ammonia or substituted ammonia under conditions such that a composition comprising second compound comprising an alcohol group is produced.

In some embodiments, the invention relates to a method comprising: i) mixing a first compound comprising an alcohol group with a compound selected from the group consisting of 6-halohexanoic acid, substituted 6-halohexanoic acid, 5-halopentanonic acid, substituted 5-halopentanonic acid, 2-haloalkylcarboxylic acid, substituted 2-haloalkylcarboxylic acid, 4-halobutyric acid, substituted 4-haloburyric acid, 3-halopropionic acid, and substituted 3-halopropionic acid under conditions such that a haloalkyl ester is produced; ii) mixing said haloalkyl ester with a chiral compound under conditions such that a first diastereomer and a second diastereomer are formed; iii) separating said first diastereomer and said second diastereomer under conditions such that a composition comprising first diastereomer of greater than 80% purity by weight is produced, and iii) mixing said separated halogenated alkyl ester isomer with ammonia or substituted ammonia under conditions such that a composition comprising a compound comprising an alcohol group is produced.

In some embodiments, the invention is a method comprising: i) mixing a first compound comprising an alcohol group with phosphorus pentoxide and a compound selected from the group consisting of 6-halohexanoic acid, substituted 6-halohexanoic acid, 5-halopentanonic acid, substituted 5-halopentanonic acid, 4-halobutyric acid, substituted 4-halobuyric acid, 3-halopropionic acid, substituted 3-halopropionic acid, 2-haloethanoic acid, or substituted 2-haloethanoic acid under conditions such that a haloalkyl ester is produced; ii) mixing said haloalkyl ester with a chiral compound under conditions such that a first diastereomer and a second diastereomer are formed; iii) separating said first diastereomer and said second diastereomer under conditions such that an enriched composition is produced comprising said first diastereomer and said second diastereomer, wherein said first diastereomer is greater than 80% of the molecules comprising said first diastereomer and said second diastereomer, and iii) mixing said enriched composition with ammonia or substituted ammonia under conditions such that a composition comprising a compound comprising a alcohol group is produced.

In some embodiments, the invention relates to a composition comprising a purified isomer or the following formula:

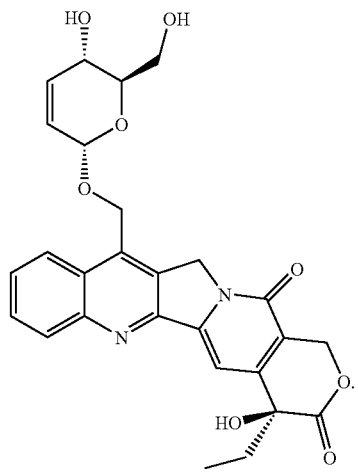

In some embodiments, the invention relates to a purified alpha-linked isomer of HAR-7 in substantially crystalline form essentially free from beta-linked isomer, and having a purity of at least 95% by mass aside from residual solvents.

In some embodiments, the invention relates to a composition comprising a purified alpha-linked isomer of HAR-7 essentially free from beta-linked isomer having a purity of at least 95% by mass aside from residual solvents. In other embodiments, it is a composition of HAR-7 having substantially the same $^1$H-NMR spectra as set out in FIG. 8. In further embodiments, the composition comprises a compound having an $^1$H-NMR with peaks consisting essentially of those provided in FIG. 8. In other embodiments, it is a composition of 7-[4'S,5'R-4',6'-di-O-acetyl-2',3'dideoxy-alpha-D-erythro-hex-2'-enopyranosyl]-oxymethyl camptothecin 20-(4-bromo)-n-butyrate having substantially the same $^1$H-NMR spectra as set out in FIG. 7. In further embodiments, the composition comprises a compound having an $^1$H-NMR with peaks consisting essentially of those provided in FIG. 7. In further embodiments, the composition having an $^1$-NMR with peaks consisting essentially of 0.99 (dd, J=7.4, 7.4 Hz, 3H), 2.07 (3H), 2.09 (3H), 2.19 (dd, J=6.7, 6.7 Hz, 2H), 2.23-2.33 (m, 2H), 2.68 (1H) and 2.74 (1H) (ABq, J$_{AB}$=16.5 Hz, the 2.68 peaks are further split into dd with J=6.7, 6.7 Hz and the 2.74 peaks further split into dd with J=6.7, 6.7 Hz), 3.45 (dd, J=6.3, 6.3 Hz, 2H), 4.04-4.12 (m, 3H), 5.22 (1H) and 5.53 (1H) (ABq, J$_{AB}$=13.5 Hz, the 5.22 peaks are further split into d with J=2.2 Hz), 5.30-5.48 (m, 4H), 5.38 (1H) and 5.68 (1H) (ABq, J$_{AB}$=17.3 Hz), 5.92 (1H) and 5.98 (1H) (ABq, $J_{AB}$=10.3 Hz, the 5.92 peaks are further split into dd with J=2.2, 1.9 Hz), 7.20 (s, 1H), 7.68 (dd, J=8.4, 7.2 Hz, 1H), 7.83 (dd, J=8.4, 7.2 Hz, 1H), 8.07 (d, J=8.4 Hz, 1H), 8.23 (d, J=8.4 Hz, 1H) shifted from tetramethyl silane in a solvent of CDCl$_3$.

In one embodiment, the present invention contemplates a composition comprising a purified camptothecin saccaride compound isomer of the following formula:

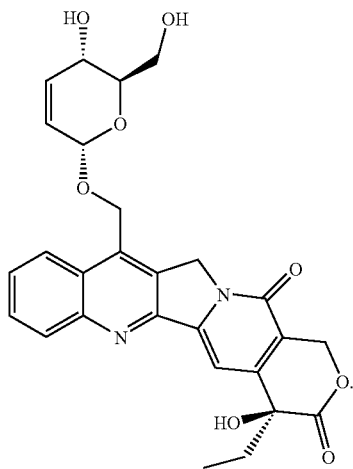

In one embodiment, the purified isomer is greater than 50% by weight of camptothecin saccharide component. In one embodiment, the purified isomer is greater than 70% by weight of camptothecin saccharide component. In one embodiment, the purified isomer is greater than 90% by weight of camptothecin saccharide component. In one embodiment, the purified isomer is greater than 99.5% by weight of camptothecin saccharide component.

In one embodiment, the present invention contemplates, a composition comprising a purified alpha-linked isomer of HAR-7 essentially free from beta-linked isomer having a purity of at least 95% by mass aside from residual solvents. In one embodiment, the HAR-7 has substantially the same $^1$H-NMR spectra as set out in FIG. 8.

In one embodiment, the present invention contemplates a composition of 7-[4'S,5'R-4',6'-di-O-acetyl-2',3'-dideoxy-D-erythro-hex-2'-enopyranosyl]-oxymethyl camptothecin 20-(4-bromo)-n-butyrate comprising an $^1$H-NMR spectra as set out in FIG. 7. In one embodiment, the composition has an $^1$H-NMR with peaks consisting essentially of those provided in FIG. 7.

DEFINITIONS

Figure 1:
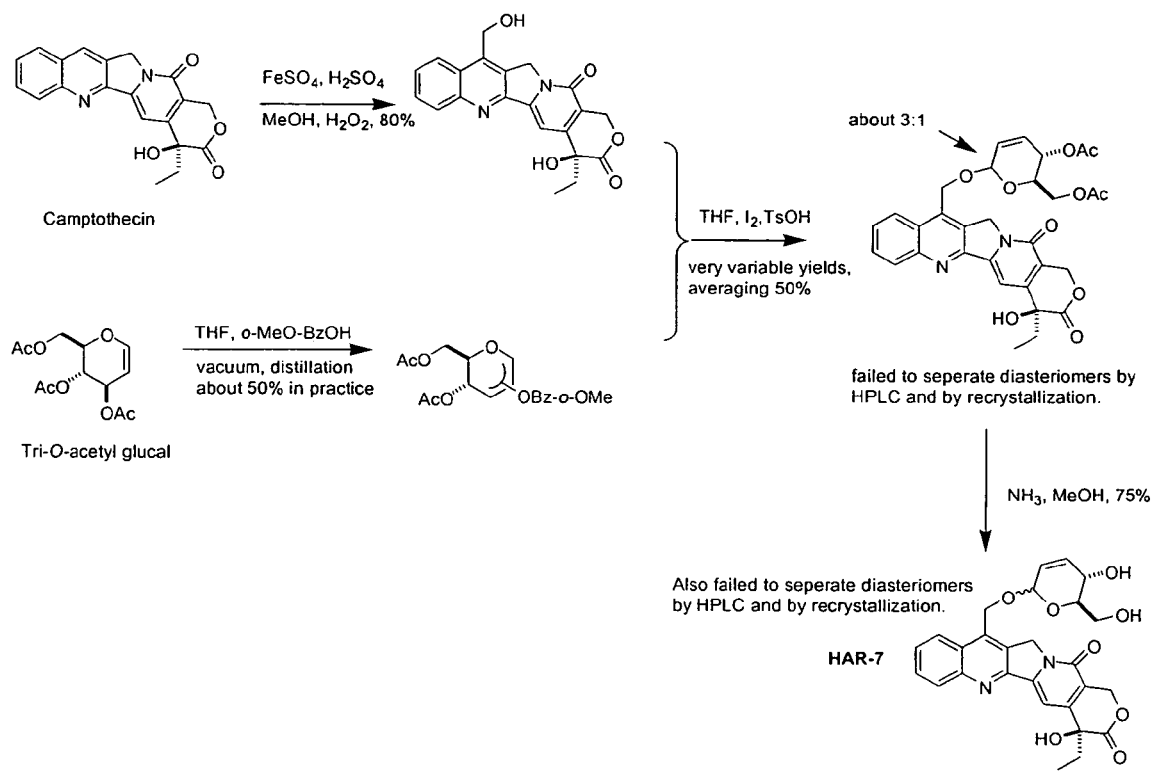
FIG. 1. Method of making HAR-7, glycosylated 7-hydroxymethyl camptothecin.

A chemical group is "absent" means that no atom is connected such that the bond does not exists or is connected to the corresponding next atom or chemical group. For example, if a carbon atom in a phenyl ring is replaced with a nitrogen atom, the hydrogen atom that was attached to the carbon atom may be absent.

"Acyl" means an —C(=O)alkyl or —C(=O)aryl group.

"Acyloxy" means —O-acyl.

"Adverse drug reaction" means any response to a drug that is noxious and unintended and occurs in doses for prophylaxis, diagnosis, or therapy including side effects, toxicity, hypersensitivity, drug interactions, complications, or other idiosyncrasy. Side effects are often adverse symptom produced by a therapeutic serum level of drug produced by its pharmacological effect on unintended organ systems (e.g., blurred vision from anticholinergic antihistamine). A toxic side effect is an adverse symptom or other effect produced by an excessive or prolonged chemical exposure to a drug (e.g., digitalis toxicity, liver toxicity). Hypersensitivities are immune-mediated adverse reactions (e.g., anaphylaxis, allergy). Drug interactions are adverse effects arising from interactions with other drugs, foods or disease states (e.g., warfarin and erythromycin, cisapride and grapefruit, loperamide and Clostridium difficile colitis). Complications are diseases caused by a drug (e.g., NSAID-induced gastric ulcer, estrogen-induced thrombosis). The adverse drug reaction may be mediated by known or unknown mechanisms (e.g., Agranulocytosis associated with chloramphenicol or clozapine). Such adverse drug reaction can be determined by subject observation, assay or animal model well-known in the art.

"Alkyl" means a straight chain or branched, noncyclic or cyclic, unsaturated or saturated aliphatic hydrocarbon containing from 1 to 10 carbon atoms, while the term "lower alkyl" has the same meaning as alkyl but contains from 1 to 6 carbon atoms. The term "higher alkyl" has the same meaning as alkyl but contains from 2 to 10 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Cyclic alkyls are also referred to herein as "homocycles" or "homocyclic rings." Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"Alkylamino" and "dialkylamino" mean one or two alkyl moiety attached through a nitrogen bridge (i.e., —N-alkyl) such as methylamino, ethylamino, dimethylamino, diethylamino, and the like.

"Alkyl carboxylate ester" means an ester with an alky group (i.e., —OC(=O)-alkyl)

"Alkoxy" means an alkyl moiety attached through an oxygen bridge (i.e., —O-alkyl) such as methoxy, ethoxy, and the like.

"Alkylthio" means an alkyl moiety attached through a sulfur bridge (i.e., —S-alkyl) such as methylthio, ethylthio, and the like.

"Alkylsulfonyl" means an alkyl moiety attached through a sulfonyl bridge (i.e., —SO2-alkyl) such as methylsulfonyl, ethylsulfonyl, and the like.

"Alpha-isomer" means a sugar attached through an oxygen bridge to another atomic structure such that the oxygen of the oxygen bridge on the first carbon and the methylene on the fifth carbon (or fourth carbon if the sugar is a five membered ring, ect.) have a trans confirmation; for example,

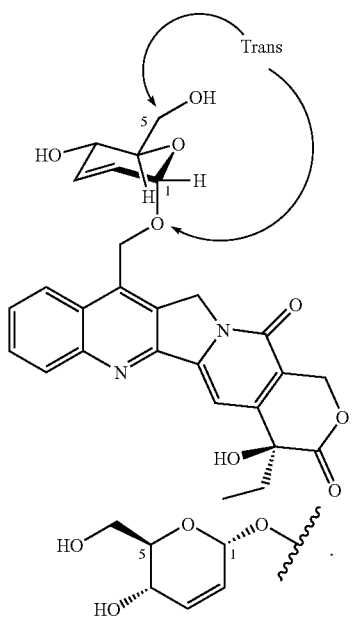

"Aryl" means an aromatic carbocyclic moiety such as phenyl or naphthyl.

"Arylalkyl" means an alkyl having at least one alkyl hydrogen atoms replaced with an aryl moiety, such as benzyl, —(CH$_2$)$_2$phenyl, —(CH$_2$)$_3$phenyl, —CH(phenyl)$_2$, and the like.

"Beta-isomer" means a sugar attached through an oxygen bridge to another atomic structure such that the oxygen of the oxygen bridge on the first carbon and the methylene on the fifth carbon (or fourth carbon if the sugar is a five membered ring, ect.) has a cis confirmation; for example:

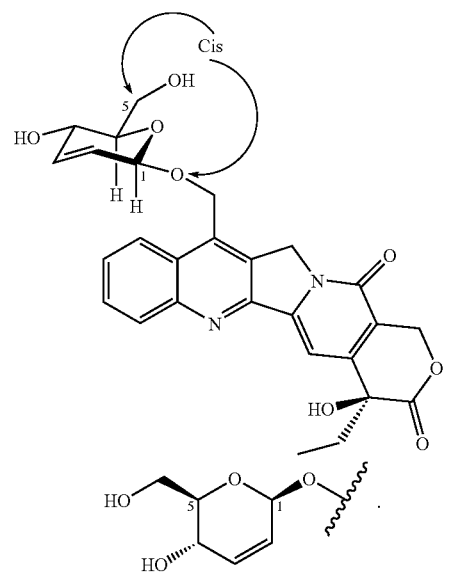

"Camptothecin compound" or molecules, and the like means substituted or unsubstituted compounds of the following formula:

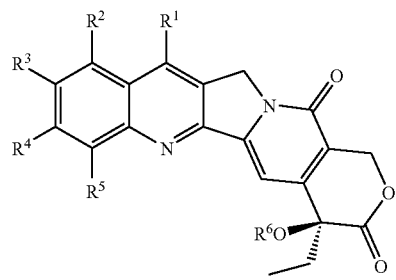

wherein, $R^1$, $R^2$, $R^3$, $R^4$, and $R^5$ are the same or independently and individually hydrogen, alkyl, substituted alkyl, alkoxy, or substituted alkoxy; $R^6$ is hydrogen, acyl, substituted acyl, alkyl or substituted alkyl.

"Camptothecin Saccharide" compounds, molecules, and the like means substituted or unsubstituted compounds of the following formula:

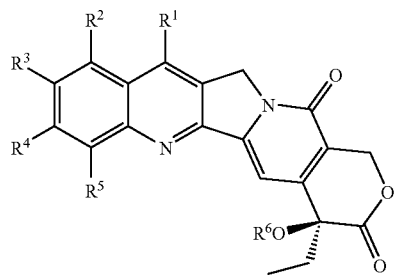

wherein, $R^1$, $R^2$, $R^3$, $R^4$, and $R^5$ are the same or independently and individually hydrogen, alkyl, substituted alkyl, alkoxy, substituted alkoxy, or a —[X(CH$_2$)$_n$Y]$_m$-Sacharride group;

$R^6$ is hydrogen, acyl, substituted acyl, alkyl or substutited alkyl;

X and Y are the same or independently and individually sulfur, oxygen, nitrogen, or absent;

n is 1 to 100;

m is 1 to 100.

As used herein, the term "camptothecin saccharide component" refers that part of a composition that contains all of camptothecin saccharide molecules in a given composition, including all conformational and stereomeric forms. In preferred embodiments, a given compound (e.g. designated by a structure) makes up a large percentage (e.g. by number of molecules and/or by weight) of the camptothecin saccharide component. For example, a given camptothecin saccharide derivative may be present in an aqueous composition at a level where 70% of all the camptothecin saccharide components are of that given compound (e.g. alpha-linked isomer), while most of the composition itself is composed of water.

A "coupling catalyst" means a molecular entity that temporarily interacts with a molecule after displacing a leaving group until the entity is itself displaced by a nucleophile. For example, pyridine or dimethylamino pyridine are routinely uses as carboxylic acid coupling catalyst because the pyridine reacts with activated carbonyls and is itself displaced by other nucleophiles (i.e., alcohols, amines, etc.)

"Diastereomers" are stereoisomers that are not enantiomers (i.e., mirror images of each other). The term is intended to include salts formations (e.g., tartaric acid salts). Diastereomers can have different physical properties and different reactivity.

"Enantiomeric excess" (ee) refers to the products that are obtained by a synthesis comprising an enantioselective step, whereby a surplus of one enantiomer in the order of at least about 52% ee is obtained.

"Exposing" or "deprotecting" a first atom, and the like, means breaking chemical bonds between the first atom and a second atom in a chemical structure intended to prevent modification of the first atom until exposure to a selected deprotecting reagent.

"Halogen" means fluoro, chloro, bromo and iodo.

"Haloalkyl" means an alkyl having at least one hydrogen atom replaced with halogen, such as trifluoromethyl and the like.

"Haloalkyl carboxylate ester" means an alkyl carboxylate ester wherein alkyl is a haloalkyl.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —$CH_2$pyridinyl, —$CH_2$pyrimidinyl, and the like.

"Heterocycle" (also referred to herein as a "heterocyclic ring") means a 4- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocycle alkyl" means an alkyl having at least one alkyl hydrogen atom replaced with a heterocycle, such as —$CH_2$morpholinyl, and the like.

"Homocycle" (also referred to herein as "homocyclic ring") means a saturated or unsaturated (but not aromatic) carbocyclic ring containing from 3-7 carbon atoms, such as cyclopropane, cyclobutane, cyclopentane, cyclohexane, cycloheptane, cyclohexene, and the like.

"Isomers" means any of two or more substances that are composed of the same elements in the same proportions but differ in the three dimensional arrangement of atoms including enantiomeric (i.e., mirror images) and diastereomeric isomers.

The term "manage" when used in connection with a disease or condition means to provide beneficial effects to a patient being administered with a prophylactic or therapeutic agent, which does not result in a cure of the disease. In certain embodiments, a patient is administered with one or more prophylactic or therapeutic agents to manage a disease so as to prevent the progression or worsening of the disease.

"Methylene" means —$CH_2$—.

As used herein and unless otherwise indicated, the term "prodrug" means a derivative that can hydrolyze, oxidize, or otherwise react under biological conditions (in vitro or in vivo) to provide an active compound. Examples of prodrugs include, but are not limited to, derivatives and metabolites that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, prodrugs of compounds with carboxyl functional groups are the lower alkyl esters of the carboxylic acid. If present, esterifying any of the carboxylic acid moieties present on the molecule conveniently forms the carboxylate esters.

"Pharmaceutically active derivative" refers to any compound that upon administration to the recipient is capable of providing directly or indirectly, the activity disclosed herein.

"Pharmaceutically acceptable salts or "complexes" refers to salts or complexes of the below-identified compounds that retain the desired biological activity. Examples of such salts include, but are not restricted to acid addition salts formed with inorganic acids (e.g. hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, poly glutamic, acid, naphthalene sulfonic acid, naphthalene disulfonic acid, and poly galacturonic acid. Said compounds can also be administered as pharmaceutically acceptable quaternary salts known by a person skilled in the art, which specifically include the quaternary ammonium salts of the formula —$NR,R',R''^+Z^-$, wherein R, R', R'' is independently hydrogen, alkyl, or benzyl, and Z is a counter ion, including chloride, bromide, iodide, alkoxide, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

As used herein, the terms "prevent" and "preventing" include the prevention of recurrence, spread or onset. It is not intended that the present invention be limited to complete prevention. In some embodiments, the onset is delayed, or the severity of the disease is reduced.

As used herein, the terms "purified isomer" and "purified isomer composition" are meant to indicate a composition (e.g. derived from a racemic mixture or synthesized de novo) wherein one isomer has been enriched (e.g., alpha-isomer) over the other (e.g., beta-isomer), and more preferably, wherein the other isomer represents less than 10%, and more preferably less than 7%, and still more preferably, less than 2% of the preparation. Purified compositions in accordance with the invention preferably contain less than 5% mass/mass (m/m), advantageously less than 3% m/m, of impurities. It is to be understood that references herein to "impurities" are to be understood as to include unwanted reaction products that are not isomers formed during synthesis and does not include residual solvents remaining from the process used in the preparation of the composition or excipients used in pharmaceutical preparations.

The expression "essentially free" of a molecule means that the molecule is present in a composition only as an unavoidable impurity.

The term "crystalline form" means the composition contains a structure whereby molecules are arranged in a substantially regularly repeating order.

"Saccharide" means a sugar or substituted sugar exemplified by but is not limited to 2,3-dideoxyhex-2-enopyranoside, 2,3-desoxy-2,3-dehydroglucose, 2,3-desoxy-2,3-dehydroglucose diacetate, glucoside, glucoside tetraacetate, mannoside, mannoside tetraacetate, galactoside, galactoside tetraacetate, alloside, alloside tetraacetate, guloside, guloside tetraacetate, idoside, idoside tetraacetate, taloside, taloside tetraacetate, rhamnoside, rhamnoside triacetate, maltoside, maltoside heptaacetate, 2,3-desoxy-2,3-dehydromaltoside, 2,3-desoxy-2,3-dehydromaltoside pentaacetate, 2,3-desoxymaltoside, lactoside, lactoside tetraacetate, 2,3-desoxy-2,3-dehydrolactoside, 2,3-desoxy-2,3-dehydrolactoside pentaacetate, 2,3-desoxylactoside, glucouronate, N-acetylglucosamine, including polysaccharides (i.e., polyol or compounds having a large ratio of primary and secondary protected or unprotected hydroxyl groups where if unprotected have a ratio of hydrogen to carbon atoms near 2:1). Saccharides can be derivatized with molecular arrangements that facilitate production (i.e., contain a protecting group, e.g., acetyl group). Saccharides can be derivatized to form prodrugs.

"Subject" means any animal, preferably a human patient, livestock, or domestic pet.

The term "substituted" as used herein means any of the above groups (i.e., alkyl, aryl, arylalkyl, heteroaryl, heteroarylalkyl, homocycle, heterocycle and/or heterocycle alkyl) wherein at least one hydrogen atom is replaced with a substituent. In the case of an oxo substituent ("=O"), two hydrogen atoms are replaced. When substituted one or more of the above groups are substituted, "substituents" within the context of this invention include halogen, hydroxy, oxo, cyano, nitro, amino, alkylamino, dialkylamino, alkyl, alkoxy, alkylthio, haloalkyl, aryl, arylalkyl, heteroaryl, heteroarylalkyl, heterocycle and heterocycle alkyl, as well as a saccharide, $-NR_aR_b$, $-NR_aC(=O)R_b$, $-NR_aC(=O)NR_aNR_b$, $-NR_aC(=O)OR_b$, $-NR_aSO_2R_b$, $-C(=O)R_a$, $C(=O)$ $OR_a$, $-C(=O)NR_aR_b$, $-OC(=O)NR_aR_b$, $-OR_a$, $-SR_a$, $-SOR_a$, $-S(=O)_2R_a$, $-OS(=O)_2R_a$ and $-S(=O)_2OR_a$.

In addition, the above substituents may be further substituted with one or more of the above substituents, such that the substituent substituted alky, substituted aryl, substituted arylalkyl, substituted heterocycle or substituted heterocycle alkyl. $R_a$ and $R_b$ in this context may be the same or different and independently hydrogen, alkyl, haloalkyl, substituted alkyl, aryl, substituted aryl, arylalkyl, substituted arylalkyl, heterocycle, substituted heterocycle, heterocycle alkyl or substituted heterocycle alkyl.

As used herein, the terms "treat" and "treating" are not limited to the case where the subject (e.g. patient) is cured and the disease is eradicated. Rather, the present invention also contemplates treatment that merely reduces symptoms, and/or delays disease progression.

To "modify" a compound means to either add a new chemically bonded atom to said compound, eliminate an atom or group or atoms from the compound, and/or reducing or oxidizing the atomic hybridization state (i.e., $sp^2$ to an $sp^3$, reduction, or $sp^3$ to an sp, oxidation) of an atom or group of atoms in the compound.

A "nucleophile" (or nucleophilic reagent) is a reagent that forms a bond to its reaction partner by donating bonding electrons.

DETAILED DESCRIPTION OF THE INVENTION

The present invention relates to compositions and methods for preparing pharmaceutical compositions. In some embodiments, the invention includes compounds and methods of resolving chiral compounds. In some embodiments, the invention includes chiral and crystalline compositions and hydrates. In some embodiments, the invention contemplates compositions comprising camptothecin derivatives and synthetic intermediates thereof. In some embodiments, the invention includes methods of protecting, inserting, modifying, separating isomers, and removing chemical groups.

Isolated in 1966 from the Chinese tree *Camptotheca acuminata*, camptothecin was found to have significant efficacy in animal tumor models. Upon advancement to human clinical studies, camptothecin was found to have mixed results in fighting tumor growth and possessed side effects ranging from vomiting and diarrhea to myelosuppression and hemorrhagic cystitis. It is believed that camptothecin has a unique mechanism of action, i.e., via topoisomerase I DNA damage by binding and stabilizing a covalent DNA-topoisomerase I complex in which one of the DNA strands is broken. Among the formidable challenges facing any effort to develop the potential anticancer properties of camptothecin into a useable treatment are clearly the problems of drug delivery and toxicity.

Camptothecin was used as a control to test the anti-cancer efficacy of the novel camptothecin analogs of the present invention. Two types of in vitro assays were used to measure the effectiveness of both unmodified camptothecin and the analogs of the present invention: first, the compound of interest was utilized in the well-established topoisomerase I assay, to determine the degree to which the drug inhibited the activity of topoisomerase I; second, the compound of interest may be tested to determine the inhibition of cell growth for several different cell lines (HT-29: human colon tumor, MCF-7: human breast tumor, B16: murine melanoma, P388: murine leukemia, P388/CPT: CPT-resistant murine leukemia cells).

The topoisomerase I catalytic activity may be measured by converting the supercoiled SV40 DNA (Form I) to the relaxed form (Form $I_0$). All reactions were performed in 20 µL reaction buffer (Tris-HCl, 10 mM, pH 7.5; EDTA, 1 mM; NaCl, 100 mM) with 0.25 µg SV40 DNA, 0.5 unit of human placental topoisomerase I (TopoGen) and graded concentrations of the analog tested. The reaction mixtures were incubated at 37° C. for 30 minutes. The topoisomerase I activity was stopped by incubating the reaction mixture with 1 μL of 10% SDS and 1 μL of proteinase K (1.25 mg/mL) for additional 30 min. One μL of the loading buffer (1% bromophenol blue and 48% sucrose) was then added. Ten μL of the reaction mixture was loaded onto a 1% agarose gel prepared in TAE buffer containing 2 μg/mL chloroquine; and the electrophoresis was performed at 82 volt for 4.5 hr in the TAE buffer containing 2 .mu.g/mL chloroquine. Chloroquine is added to separate nicked and relaxed DNA molecules; without chloroquine, the fully relaxed Form $I_0$ comigrated with the nicked DNA. The gels were then stained with 0.5 μg/mL ethidium bromide solution for 30 min or longer (if chloroquine is present during the electrophoresis step), and destained with 5 changes of deionized water. DNA bands were visualized with a 254 nm ultraviolet light (Spectroline Transilluminator Model TL-254A) and documented with a Polaroid 665 positive/negative instant pack film. The DNA bands (image) on the negative were densitometrically scanned with a Molecular Dynamic Personal Densitometer. The percent inhibition of Toposiomerase I activity is calculated based on the following equation: % Inhibition=$(F_{SC(E+D)}-F_{SC(E)})/(F_{SC(C)}-F_{SC(E)}) \times 100$, where $F_{SC(E+D)}$ represents fraction of supercoiled DNA in the presence of enzyme and drug; $F_{SC(E)}$ represents fraction of supercoiled DNA in the presence of enzyme alone; $F_{SC(C)}$ represents fraction of supercoiled DNA in the untreated SV40 DNA; the $IC_{50}$ value was estimated using the same four-parameter logistic equation described in the in vitro growth inhibition studies.

The references Shull et al., U.S. Pat. No. 5,677,286, Shull et al., U.S. Pat. No. 5,932,709, which are both hereby incorporated by reference, disclose camptothecin saccharide derivatives and methods of making producing said derivatives using activated saccharide glycals. These methods utilize 20-hydroxymethyl camptothecin as an intermediate. (see FIG. 1) Glycosylation of 20-hydroxymethyl camptothecin has disadvantages because 20-hydroxymethyl camptothecin is not substantially soluble in solvents typically used in methods to produce the corresponding glycosylated camptothecin derivatives. To this end, these references disclosed methods of using activated glycals in order to obtain the desired target compounds. However, using these procedures have ultimately proved to be undesirable because obtaining consistent yields of particular diastereomerically pure compositions has been elusive. The products obtained from these procedures result in diastereomeric mixtures in which the Applicant has not been able to entirely separate using procedures previously described or methods routinely used in the art. For example, using the procedure provided in Shull et al., U.S. Pat. No. 5,677,286, Shull et al., U.S. Pat. No. 5,932,709, the camptothecin saccharide derivatives having the following formula:

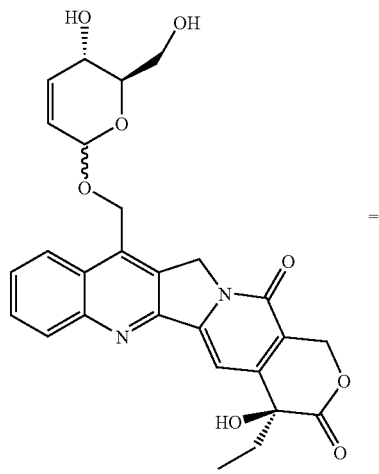

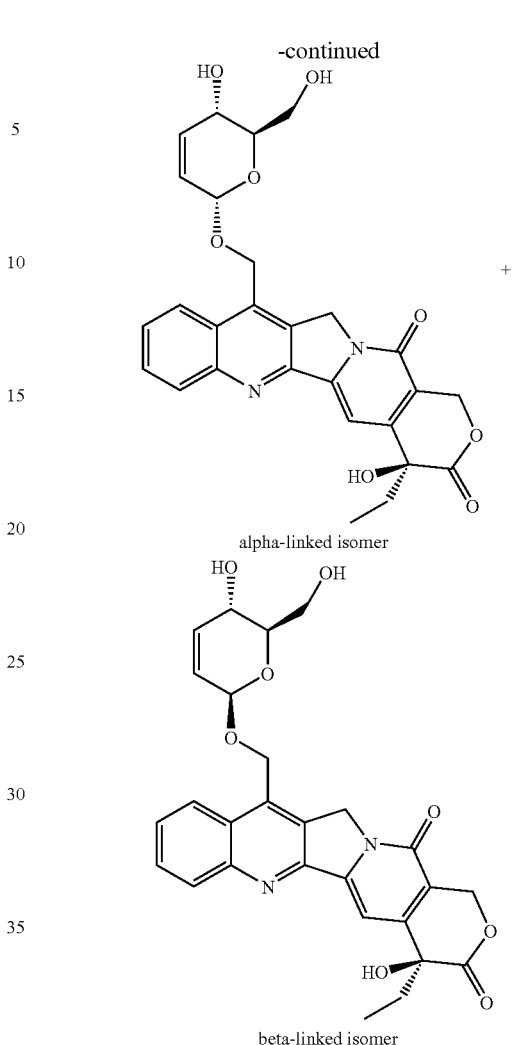

alpha-linked isomer beta-linked isomer were obtained as a composition containing approximately a 3:1 mixture of the alpha and beta isomers respectively. Attempts to separate the alpha and beta isomers (including the protected di-acetate derivatives) to obtain a composition comprising a substantially pure form of the alpha and/or beta isomer until now have been unsuccessful.

The Applicant desired to identify an alternative method of preparing substantially diastereomerically pure compositions comprising the single diastereomers (i.e. alpha or beta isomers) of glycosylated camptothecin for purposes of clinical studies. To this end, many of the synthetic challenges in obtaining substantially diastereomerically pure compositions were hampered the inability to dissolve many camptothecin derivates in typical low boiling organic solvents. Thus, the Applicant set out to improve the solubility of synthetic intermediates by acylating the tertiary alcohol on the chiral carbon, with the intent of removing it at the end of the synthetic process. Preferentially, this protecting group is sufficiently stable to allow appropriate modification of other areas of the camptothecin molecule, and has properties that allow it to be removed under conditions compatible with other protecting groups used in the synthetic process (e.g., when removing protecting groups on the sugar moiety).

To this end, the Applicant initially attempted to utilize camptothecin tertiary hydroxy esters of hexanoic acid in order to identify diastereomeric intermediates that could be separated from one another. The synthesis of 4(S)-Ethyl-4-hexanoyl-1H-pyrano-[3',4':6,7]indolizino[1,2-b]quinoline-3,14(4H,12H)-dione:

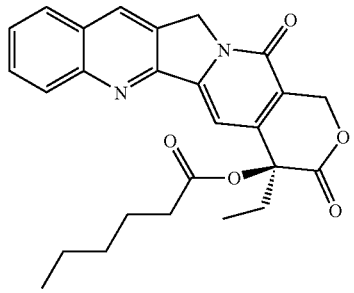

was previously described in U.S. Pat. No. 5,932,709, however, the synthetic yields were relatively low and unpredictable when done in large quantities. To this end, the Applicant has identified an improved robust method of preparing 4(S)-ethyl-4-hexanoyl-1H-pyrano-[3',4':6,7]indolizino[1,2-b]quinoline-3,14(4H,12H)-dione where hexanoic acid is mixed with camptothecin in the presence of sulfuric acid, phosphorus pentoxide, and dichloromethane to provide the desired compound in superior yields. Previous reported procedures using acid chlorides required heating the mixtures for several hours in order to obtain the desired ester. The previously described procedures also required a purification step that entailed the use of silica gel flash chromatograph. The current embodiments do not require heating for extended periods of time at elevated temperatures. Additionally, the desired intermediates are obtained in superior yields.

Hydroxymethylation of camptothecin hexanoate followed by glycosylation afforded a compound (see FIG. 2) of the following formula:

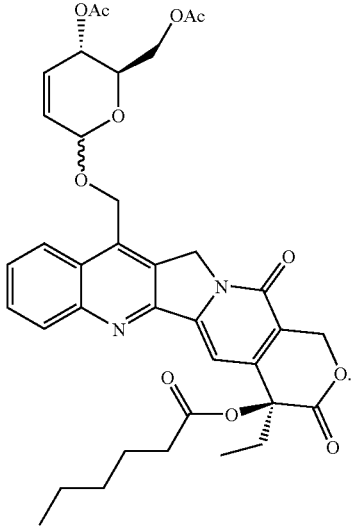

However, the compounds in this composition were again obtained as diastereomeric mixtures (about 3:1 alpha and beta isomer respectively) that where not separable using routine methods. No isomeric separation procedure is described in U.S. Pat. No. 5,932,709 In order to obtain the desired camptothecin derivative (i.e., HAR-7) it is desirable to be able to hydrolyze all of the ester bonds in a single step under the same mild conditions. Removal of the hexanoyl group and the acetyl groups were not accomplishable under the same mild conditions. The acetyl groups of the above compound can be removed under mild conditions such as by stirring the compound in methanol, bubbling nitrogen through the solution, and allowing it to stir for several hours. However, exposing the above compound under these conditions did not result in satisfactory removal of the hexanoyl group. Removal the hexanoyl group required the inconvenient use of an increased pressure and heat resulting in lower yields of the desired free hydroxyl compounds.

Because of these disadvantages, the Applicant embarked to discover alternative procedures using mild conditions and that could provide substantially diastereomerically-enriched derivatives. To this end, the Applicant attempted to create camptothecin hydroxy esters of 2-bromobutyric acid ester intermediates. Because the 2-bromobutyric acid contains a chiral carbon, it was thought that the creation of additional diastereomers may facilitate isomer separation by chromatography. A composition comprising compounds of the following formula was obtained:

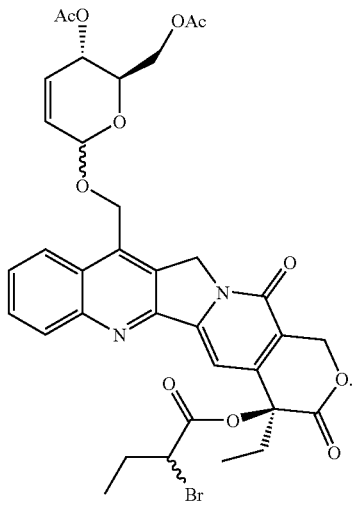

For the purposes of obtaining free hydroxyl compound, both the acetyl and 2-bromobutanoyl groups were removed using mild ammonia conditions. Unfortunately, the Applicant again failed to separate and isolate a composition comprising a single isomer from the diastereomeric mixtures.

Figure 4:
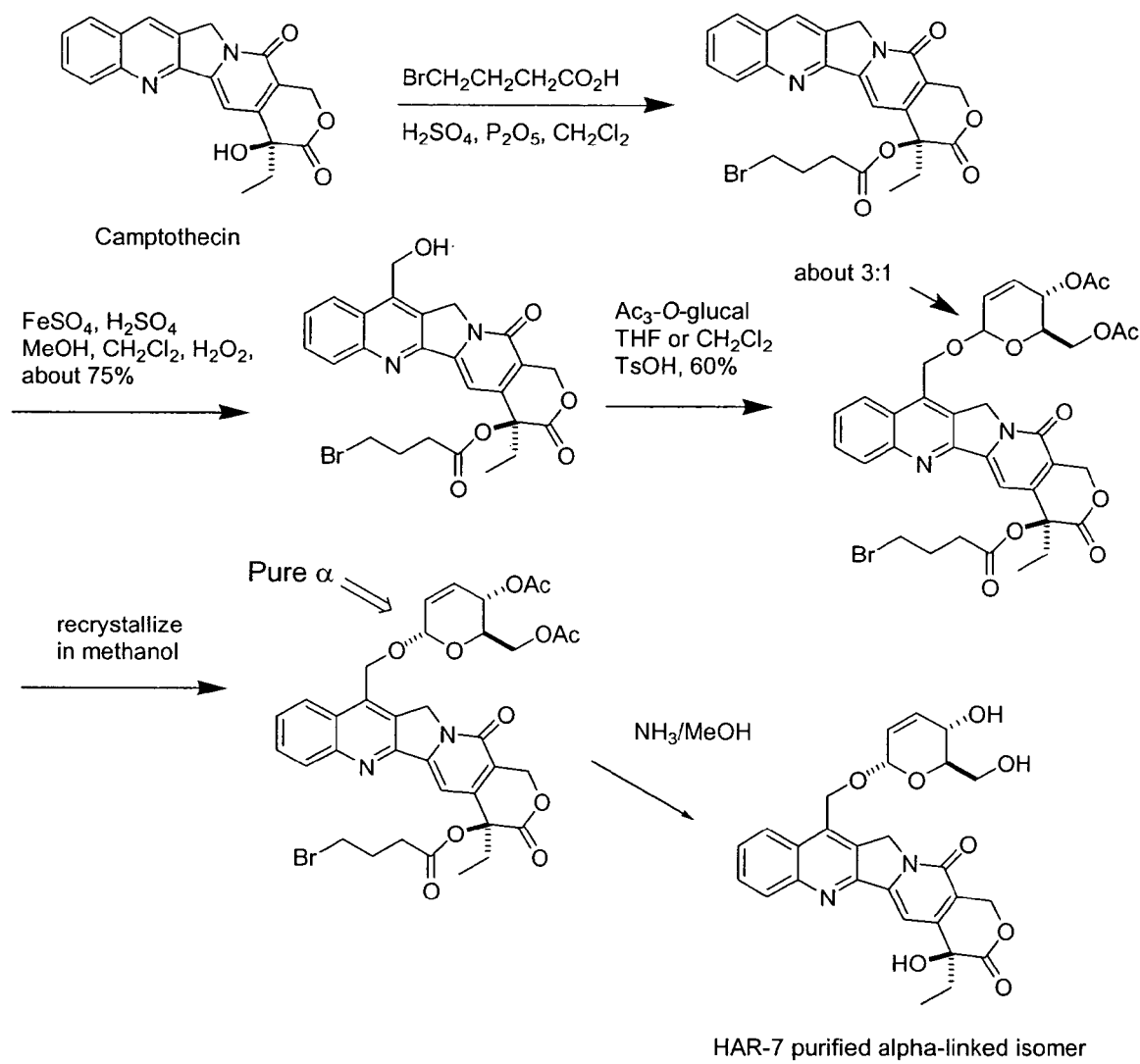
FIG. 4. Method for making HAR-7 using 4-bromo butyric acid.

Because of the inability to resolve the desired isomers, the Applicant embarked to discover alternative procedures using mild conditions and that could provide substantially diastereomerically-enriched derivatives. To this end, the Applicant attempted to create camptothecin hydroxy esters of 4-bromobutyric acid ester intermediates that could be separated from one another (FIG. 4). A composition comprising compounds of the following formula were obtained:

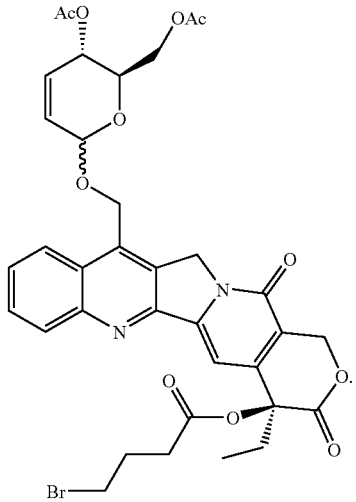

Using a recrystallization process, the Applicant was able to obtain a composition comprising a substantially pure form of the alpha-linked isomer, as depicted by the formula below:

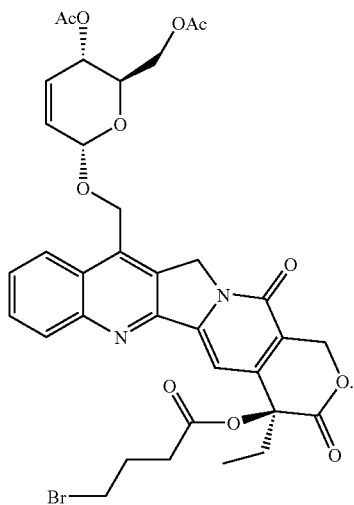

Additionally, the Applicant was able to hydrolyze both the acetyl and gama-bromo hexanoyl group under mild conditions using ammonia to obtain substantially pure forms of alpha-linked isomer having the following formula:

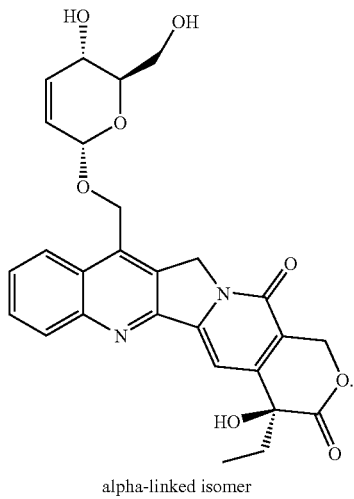

alpha-linked isomer

Pharmaceutical Formulations

The compositions comprising the active compound include bulk-drug compositions useful in the manufacture of pharmaceutical compositions (e.g., impure or non-sterile compositions) and pharmaceutical compositions (i.e., compositions that are suitable for administration to a patient) that can be used in the preparation of unit dosage forms. Such compositions optionally comprise a prophylactically or therapeutically effective amount of a prophylactic and/or therapeutic agent disclosed herein or a combination of those agents and a pharmaceutically acceptable carrier. Preferably, compositions of the invention comprise a prophylactically or therapeutically effective amount of the active compound and another therapeutic or prophylactic agent, and a pharmaceutically acceptable carrier. These compositions may contain between 0.1-99% of the active ingredient In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the active compound is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents can be used. When administered to a patient, the pharmaceutically acceptable vehicles are preferably sterile. Water can be the vehicle when the active compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propyleneglycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155).

In a preferred embodiment, the active compound and optionally another therapeutic or prophylactic agent are formulated in accordance with routine procedures as pharmaceutical compositions adapted for intravenous administration to human beings. Typically, the active compound for intravenous administration are solutions in sterile isotonic aqueous buffer. Where necessary, the compositions can also include a solubilizing agent. Compositions for intravenous administration can optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the active compound is to be administered by infusion, it can be dispensed, for example, with an infusion bottle containing sterile pharmaceutical grade water or saline. Where the active compound is administered by injection, an ampoule of sterile water for injection or saline can be provided so that the ingredients can be mixed prior to administration.

Compositions for oral delivery can be in the form of tablets, lozenges, aqueous or oily suspensions, granules, powders, emulsions, capsules, syrups, or elixirs, for example. Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for an orally administered of the active compound. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate can also be used. Oral compositions can include standard vehicles such as mannitol, lactose, starch, magnesium stearate, sodium saccharine, cellulose, magnesium carbonate, and the like. Such vehicles are preferably of pharmaceutical grade.

Further, the effect of the active compound can be delayed or prolonged by proper formulation. For example, a slowly soluble pellet of the active compound can be prepared and incorporated in a tablet or capsule. The technique can be improved by making pellets of several different dissolution rates and filling capsules with a mixture of the pellets. Tablets or capsules can be coated with a film that resists dissolution for a predictable period of time. Even the parenteral preparations can be made long-acting, by dissolving or suspending the compound in oily or emulsified vehicles which allow it to disperse only slowly in the serum.

Pharmaceutical compositions for use in accordance with the present invention can be formulated in conventional manner using one or more physiologically acceptable carriers or excipients.

Thus, the compound and optionally another therapeutic or prophylactic agent and their physiologically acceptable salts and solvates can be formulated into pharmaceutical compositions for administration by inhalation or insufflation (either through the mouth or the nose) or oral, parenteral or mucosol (such as buccal, vaginal, rectal, sublingual) administration. In one embodiment, local or systemic parenteral administration is used.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound.

For buccal administration the pharmaceutical compositions can take the form of tablets or lozenges formulated in conventional manner.

For administration by inhalation, the pharmaceutical compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

The pharmaceutical compositions can be formulated for parenteral administration by injection, e.g., by bolus injection or continuous infusion. Formulations for injection can be presented in unit dosage form, e.g., in ampoules or in multi-dose containers, with an added preservative. The pharmaceutical compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The pharmaceutical compositions can also be formulated in rectal compositions such as suppositories or retention enemas, e.g., containing conventional suppository bases such as cocoa butter or other glycerides.

In addition to the formulations described previously, the pharmaceutical compositions can also be formulated as a depot preparation. Such long acting formulations can be administered by implantation (for example subcutaneously or intramuscularly) or by intramuscular injection. Thus, for example, the pharmaceutical compositions can be formulated with suitable polymeric or hydrophobic materials (for example as an emulsion in an acceptable oil) or ion exchange resins, or as sparingly soluble derivatives, for example, as a sparingly soluble salt.

The invention also provides that a pharmaceutical composition is packaged in a hermetically sealed container such as an ampoule or sachette indicating the quantity. In one embodiment, the pharmaceutical composition is supplied as a dry sterilized lyophilized powder or water free concentrate in a hermetically sealed container and can be reconstituted, e.g., with water or saline to the appropriate concentration for administration to a patient.

In other embodiments of the invention, radiation therapy agents such as radioactive isotopes can be given orally as liquids in capsules or as a drink. Radioactive isotopes can also be formulated for intravenous injection. The skilled oncologist can determine the preferred formulation and route of administration.

The pharmaceutical compositions can, if desired, be presented in a pack or dispenser device that can contain one or more unit dosage forms containing the active ingredient. The pack can for example comprise metal or plastic foil, such as a blister pack. The pack or dispenser device can be accompanied by instructions for administration.

In certain preferred embodiments, the pack or dispenser contains one or more unit dosage forms containing no more than the recommended dosage formulation as determined in the Physician's Desk Reference (56$^{th}$ ed. 2002, herein incorporated by reference in its entirety).

Methods of administering the active compound and optionally another therapeutic or prophylactic agent include, but are not limited to, parenteral administration (e.g., intradermal, intramuscular, intraperitoneal, intravenous and subcutaneous), epidural, and mucosal (e.g., intranasal, rectal, vaginal, sublingual, buccal or oral routes). In a specific embodiment, the active compound and optionally another prophylactic or therapeutic agents are administered intramuscularly, intravenously, or subcutaneously. The active compound and optionally another prophylactic or therapeutic agent can also be administered by infusion or bolus injection and can be administered together with other biologically active agents. Administration can be local or systemic. The active compound and optionally the prophylactic or therapeutic agent and their physiologically acceptable salts and solvates can also be administered by inhalation or insufflation (either through the mouth or the nose). In a preferred embodiment, local or systemic parenteral administration is used.

In specific embodiments, it can be desirable to administer the active compound locally to the area in need of treatment. This can be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as silastic membranes, or fibers. In one embodiment, administration can be by direct injection at the site (or former site) of an atherosclerotic plaque tissue.

Pulmonary administration can also be employed, e.g., by use of an inhaler or nebulizer, and formulation with an aerosolizing agent, or via perfusion in a fluorocarbon or synthetic pulmonary surfactant. In certain embodiments, the active compound can be formulated as a suppository, with traditional binders and vehicles such as triglycerides.

In another embodiment, the active compound can be delivered in a vesicle, in particular a liposome.

In yet another embodiment, the active compound can be delivered in a controlled release system. In one embodiment, a pump can be used. In another embodiment, polymeric materials can be used.

The amount of the active compound that is effective in the treatment or prevention of heart conditions can be determined by standard research techniques. For example, the dosage of the active compound which will be effective in the treatment or prevention of heart conditions can be determined by administering the active compound to an animal in a model such as, e.g., the animal models known to those skilled in the art. In addition, in vitro assays can optionally be employed to help identify optimal dosage ranges.

Selection of a particular effective dose can be determined (e.g., via clinical trials) by a skilled artisan based upon the consideration of several factors which will be known to one skilled in the art. Such factors include the disease to be treated or prevented, the symptoms involved, the patient's body mass, the patient's immune status and other factors known by the skilled artisan.

The precise dose to be employed in the formulation will also depend on the route of administration, and the seriousness of the disease-related wasting, and should be decided according to the judgment of the practitioner and each patient's circumstances. Effective doses can be extrapolated from dose-response curves derived from in vitro or animal model test systems.

The dose of the active compound to be administered to a patient, such as a human, is rather widely variable and can be subject to independent judgment. It is often practical to administer the daily dose of the active compound at various hours of the day. However, in any given case, the amount of the active compound administered will depend on such factors as the solubility of the active component, the formulation used, patient condition (such as weight), and/or the route of administration.

The general range of effective amounts of the active compound alone or in combination with another prophylactic or therapeutic agent(s) are from about 0.001 mg/day to about 1000 mg/day, more preferably from about 0.001 mg/day to 750 mg/day, more preferably from about 0.001 mg/day to 500 mg/day, more preferably from about 0.001 mg/day to 250 mg/day, more preferably from about 0.001 mg/day to 100 mg/day, more preferably from about 0.001 mg/day to 75 mg/day, more preferably from about 0.001 mg/day to 50 mg/day, more preferably from about 0.001 mg/day to 25 mg/day, more preferably from about 0.001 mg/day to 10 mg/day, more preferably from about 0.001 mg/day to 1 mg/day. Of course, it is often practical to administer the daily dose of compound in portions, at various hours of the day. However, in any given case, the amount of compound administered will depend on such factors as the solubility of the active component, the formulation used, subject condition (such as weight), and/or the route of administration.

A popular cancer drug is taxol. Typical dosage ranges of taxol include less than 10 mg to 100 mg or more. Particular doses of taxol include about 5 mg, 10 mg, 20 mg, 40 mg, 50 mg, 60 mg, 80 mg, 100 mg, 150 mg, 200 mg. Typically, these are daily dosages. Generally, higher dosages are less preferred because of potential gastric disturbances. Therapeutic dosages may range between 40 to 80 mg per day when tolerable by a patient.

The invention provides for any method of administrating lower doses of known agents (e.g., taxol) than previously thought to be useful for the prevention or treatment of cancer.

The invention provides a pharmaceutical pack or kit comprising one or more containers containing an active compound and optionally one or more other prophylactic or therapeutic agents useful for the prevention or treatment of cancer. The invention also provides a pharmaceutical pack or kit comprising one or more containers containing one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration; or instructions for the composition's use.

The present invention provides kits that can be used in the above methods. In one embodiment, a kit comprises the active compound, in one or more containers, and optionally one or more other prophylactic or therapeutic agents useful for the treatment of cancer, in one or more containers.

EXAMPLES

Example 1

Synthesis of tri-O-acetyl-D-glucal

Tri-O-acetyl-D-glucal was synthesized according to the following procedure. Alternatively it could be commercially obtained from Pfanstiehl Laboratories Inc. (Wankeyan, Ill.), however the procedure described below has the advantage of reduced cost compared to the commercial source. Glucose (1.000 g) was suspended in a solution of acetic acid (10 mL) and acetic anhydride (3.606 g, 7.0 equiv) and 1.000 g 31% HBr/acetic acid solution added. The reaction mixture was allowed to stir for 1 h, after which 9.000 g more 31% HBr/acetic acid solution (total of 7.7 equiv HBr) was added and allowed to stir overnight. Sodium acetate was then added (2.700 g) to neutralized the excess HBr, and the reaction mixture was added to a suspension containing pulverized $CuSO_4 \cdot 5H_2O$ (0.315 g), zinc (12.600 g), water (10 mL), sodium acetate (9.450 g), and acetic acid (5 mL) and the resultant reaction mixture was stirred vigorously for 1.5 h. The solution was then filtered and the solid washed with ethyl acetate (100 mL) and water (100 mL). The organic layer of the filtrate was then washed with $NaHCO_3$ (100 mL) and brine (50 mL), dried (Na₂SO₄), filtered and the solvent removed under reduced pressure to provide tri-O-acetyl-D-glucal (1.350 g, 98%) as a colorless oil Example 2

Camptothecin 20-(4-bromo)-n-butyrate

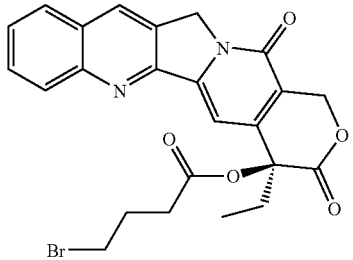

Camptothecin (25 g) and sulfuric acid (96 g) were combined and stirred until completely homogeneous. 4-Bromobutyric acid (24 g) was then added, followed by phosphorus pentoxide (44 g) in portions over the course of 1 hour and then stir overnight. The very thick and viscous reaction mixture was poured into 5 L water that was stirring vigorously. NaOH (105 grams in 1 L) was added and the resultant solid was filtered and washed with water. The crude solid was dissolved in 300 mL dichloromethane and 300 mL methanol at reflux, and then 1.5 L methanol was added to the solution and cooled to less than 0° C. Filtration and drying provided 32.5 g (91%) camptothecin 20-(4-bromo)-n-butyrate as a light tan solid: mp 235-240° C. (dec.); ¹H NMR (300 MHz, CDCl₃) δ 1.00 (dd, J=7.6, 7.6 Hz, 3H), 2.20 (dd, J=6.6, 6.8 Hz, 2H), 2.27 (m, 2H), 2.72 (m, 2H), 3.47 (dd, J=6.3, 6.3 Hz, 2H), 5.29 (s, 2H), 5.41 (1H) and 5.68 (1H) (AB q, J$_{AB}$=17.0 Hz), 7.21 (s, 1H), 7.68 (dd, J=7.3, 8.4 Hz, 1H), 7.83 (dd, J=8.5, 7.3 Hz, 1H), 7.93 (d, J=8.4 Hz, 1H), 8.22 (d, J=8.5 Hz, 1H), 8.39 (s, 1H); ¹³C NMR (75 MHz, CDCl₃) δ 7.60 (q), 27.43 (t), 31.71 (t), 32.09 (t), 32.21 (t), 49.86 (t), 66.95 (t), 75.99 (s), 95.72 (d), 119.85 (s), 127.83 (d), 127.95 (s), 127.98 (d), 128.23 (s), 129.35 (d), 130.47 (d), 130.98 (d), 145.62 (s), 146.07 (s), 148.56 (s), 152.00 (s), 157.04 (s), 167.17 (s), 171.30 (s).

Example 3

Camptothecin 20-(5-bromo)-n-pentanoate

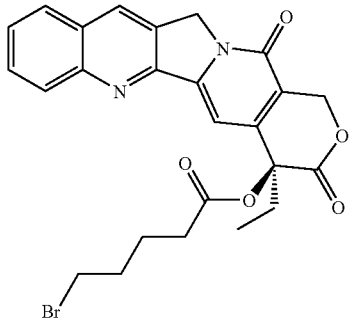

Camptothecin (2.5 g) and sulfuric acid (9.6 g) were combined and stirred until completely homogeneous. 5-Bromopentanoic acid (2.6 g) was then added, followed by phosphorus pentoxide (4.4 g) in portions over the course of 1 hour and then stir overnight. The very thick and viscous reaction mixture was poured into 500 mL water that was stirring vigorously. NaOH (11 grams in 75 mL) was added and the resultant solid was filtered and washed with water. The crude solid was dissolved in 40 mL dichloromethane and 40 mL methanol at reflux, and then 150 mL methanol was added to the solution and cooled to less than 0° C. Filtration and drying provided 3.2 g (86%) camptothecin 20-(5-bromo)-n-pentanoate as a light tan solid; ¹H NMR (300 MHz, CDCl₃) δ 0.98 (dd, J=7.4, 7.4 Hz, 3H), 1.84 (m, 2H), 1.92 (m, 2H), 2.16 (1H) and 2.28 (1H) (AB q, J$_{AB}$=14.0 Hz; both the peaks at 2.16 and 2.28 are further split into q with J=7.4), 2.55 (m, 2H), 3.40 (dd, J=7.3, 6.3 Hz, 2H), 5.28 (s, 2H), 5.40 (1H) and 5.66 (1H) (AB q, J$_{AB}$=17.3 Hz), 7.19 (s, 1H), 7.66 (dd, J=7.9, 6.9 Hz, 1H), 7.83 (dd, J=8.4, 6.9 Hz, 1H), 7.93 (d, J=7.9 Hz, 1H), 8.20 (d, J=8.4 Hz, 1H), 8.38 (s, 1H); ¹³C NMR (75 MHz, CDCl₃) δ 7.92 (q), 23.52 (t), 31.85 (t), 32.13 (t), 33.06 (t), 33.37 (t), 50.20 (t), 67.35 (t), 76.11 (s), 96.07 (d), 120.41 (s), 128.19 (d), 128.32 (s), 128.35 (d), 128.58 (s), 129.70 (d), 130.85 (d), 131.34 (d), 145.93 (s), 146.36 (s), 148.94 (s), 152.41 (s), 157.42 (s), 167.58 (s), 172.17 (s).

Example 4

7-Hydroxymethyl camptothecin 20-(4-bromo)-n-butyrate

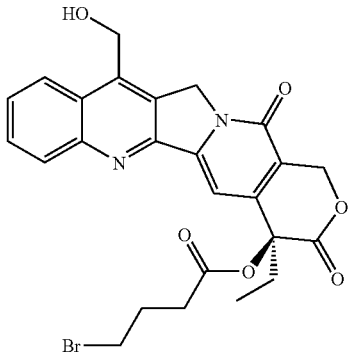

Ferrous sulfate heptahydrate (26 g) was dissolved in a minimum amount of water (ca. 13 mL) and added to a suspension of camptothecin bromobutryate (33.7 g) in methanol (2.5 L) and dichloromethane (1.5 L). Sulfuric acid (26 g) was carefully added and the entire mixture was warmed to reflux while stirring vigorously. Hydrogen peroxide (30%, 112 mL) was then added dropwise over the course of 2 hours. The solution was then concentrated to about 1 L total volume under vacuum, cooled and poured into 1.3 L water. Sodium bicarbonate was added to until the pH of the solution was in the range of 4-6. The resultant solid was filtered, washed with water and then dissolved in a minimum amount of 1:1 mixture of methanol/dichloromethane (a small amount of dark solid remains suspended in solution). The solution was then filtered through a large pad of celite, and the filtrate warmed and solvent distilled off until solid appears suspended in the solution. The solution was then cooled to 0° C. overnight and filtered and dried to give 30 g (84%) 7-hydroxymethyl camptothecin 20-(4-bromo)-n-butyrate as a light yellow solid. mp 172-176° C. (dec.); ¹H NMR (300 MHz, DMSO) δ 0.95 (dd, J=7.4, 7.2 Hz, 3H), 2.05-2.2 (m, 4H), 2.70 (dd, J=7.1 Hz, 2H); 3.33 (br s, 1H, OH), 3.56 (dd, J=6.6, 6.8 HZ, 2H), 5.21 (s, 2H), 5.30 (s, 2H), 5.49 (s, 2H), 7.02 (s, 1H), 7.62 (dd, J=7.7, 7.4 Hz, 1H), 7.78 (dd, J=7.7, 7.4 Hz, 1H), 8.07 (d, J=7.7 Hz, 1H), 8.08 (d, J=7.4 Hz, 1H); ¹³C NMR (75 MHz, DMSO) δ 7.52 (q), 2.47 (t), 30.06 (t), 31.66 (t), 33.25 (t), 50.46 (t), 59.09 (t), 66.11 (t), 75.82 (s), 94.20 (d), 118.38 (s), 123.69 (d), 124.95 (s), 126.31 (s), 127.14 (d), 129.17 (d), 129.65 (d), 142.77 (s), 145.01 (s), 145.44 (s), 147.46 (s), 151.93 (s), 156.12 (s), 166.86 (s), 170.85 (s).

Example 5

7-[4'S,5'R-4',6'-di-O-acetyl-2',3'-dideoxy-α-D-erythro-hex-2'-enopyranosyl]-oxymethyl camptothecin 20-(4-bromo)-n-butyrate

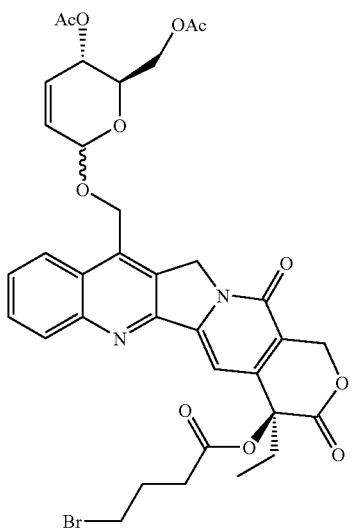

7-Hydroxymethyl camptothecin 20-(4-bromo)-n-butyrate (6.00 g), tri-O-acetyl glucal (6.00 g) and dried toluene sulfonic acid (2.20 g) was dissolved in 200 mL CH$_2$Cl$_2$ and stirred overnight. The reaction mixture was poured into 2 L CH$_2$Cl$_2$ and washed with saturated NaHCO$_3$ (1 L), brine (500 mL) and dried over Na$_2$SO$_4$. The solvent was removed under vacuum the residual solid was purified by silic gel column chromatography to give 3.0 g (36%) 3:1 α:β mixture of 7-[4'S,5'R-4',6'-di-O-acetyl-2',3'dideoxy-α-D-erythro-hex-2'-enopyranosyl]-oxymethyl camptothecin 20-(4-bromo)-n-butyrate as a light yellow solid. Recrystallization twice from methanol typically provides 2 g of pure alpha isomer. mp 158-160° C. $^1$H NMR (300 MHz, CDCl$_3$) δ 0.99 (dd, J=7.4, 7.4 Hz, 3H), 2.07 (3H), 2.09 (3H), 2.19 (dd, J=6.7, 6.7 Hz, 2H), 2.23-2.33 (m, 2H), 2.68 (1H) and 2.74 (1H) (ABq, J$_{AB}$=16.5 Hz, the 2.68 peaks are further split into dd with J=6.7, 6.7 Hz and the 2.74 peaks further split into dd with J=6.7, 6.7 Hz), 3.45 (dd, J=6.3, 6.3 Hz, 2H), 4.04-4.12 (m, 3H), 5.22 (1H) and 5.53 (1H) (ABq, J$_{AB}$=13.5 Hz, the 5.22 peaks are further split into d with J=2.2 Hz), 5.30-5.48 (m, 4H), 5.38 (1H) and 5.68 (1H) (ABq, J$_{AB}$=17.3 Hz), 5.92 (1H) and 5.98 (1H) (ABq, J$_{AB}$=10.3 Hz, the 5.92 peaks are further split into dd with J=2.2, 1.9 Hz), 7.20 (s, 1H), 7.68 (dd, J=8.4, 7.2 Hz, 1H), 7.83 (dd, J=8.4, 7.2 Hz, 1H), 8.07 (d, J=8.4 Hz, 1H), 8.23 (d, J=8.4 Hz, 1H); $^{13}$C NMR (75 MHz, CDCl$_3$) δ 7.58 (q), 20.75 (q), 20.92 (q), 27.44 (t), 31.76 (t), 32.08 (t), 32.20 (t), 50.29 (t), 62.66 (t), 64.95 (d), 65.15 (t), 67.00 (t), 67.53 (d), 75.99 (s), 94.39 (d), 95.62 (d), 119.99 (s), 123.16 (d), 125.73 (s), 126.29 (d), 126.99 (s), 128.04 (d), 130.20 (d), 130.24 (d), 130.28 (d), 138.32 (s), 145.55 (s), 145.96 (s), 148.66 (s), 152.22 (s), 157.03 (s), 167.18 (s), 169.90 (s), 170.32 (s), 171.29 (s).

Example 6

7-[4'S,5'R-2',3'dideoxy-α-D-erythro-hex-2'-enopyranosyl]-oxymethyl camptothecin

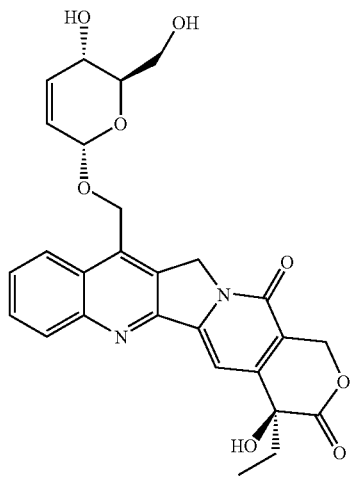

7-[4'S,5'R-4',6'-di-O-acetyl-2',3'dideoxy-α-D-erythro-hex-2'-enopyranosyl]-oxymethyl camptothecin 20-(4-bromo)-n-butyrate (0.184 g) was dissolved in 6 mL THF and 6 mL methanol and charged with 0,2 g ammonia and stirred overnight. The solvent was then removed under vacuum and silica gel column chromatography (gradient from CH$_2$Cl$_2$ to 3:1 CH2Cl$_2$:methanol) provided a solid that was then recrystallized from methanol to give 0.069 (55%) g 7-[4'S,5'R-2',3'dideoxy-α-D-erythro-hex-2'-enopyranosyl]-oxymethyl camptothecin [alpha-linked isomer of HAR-7] as a light yellow solid.

Example 7

Camptothecin 20-(2-bromo)-n-butyrate

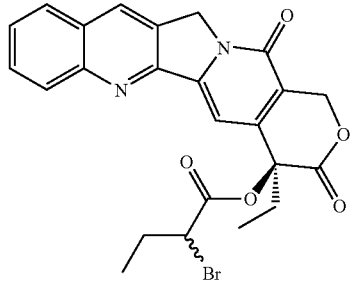

Camptothecin (5.00 g) was suspended in 20 g sulfuric acid, 10 mL CH$_2$Cl$_2$, 2-bromobutyric acid (5.00 g) after which 10 g P$_2$O$_5$ was added over the course of 1 h. The reaction mixture was stirred overnight after which it was poured into a vigorously stirred mixture of 500 mL water and 500 mL CH$_2$Cl$_2$. NaOH (20.0 g) was added, the organic layer separated and washed with NaHCO$_3$ (500 mL), brine (50 mL), dried (Na$_2$SO$_4$), filtered and the solvent removed under vacuum. The resultant solid was then recrystallized from 25% CHCl$_3$ in methanol to provide camptothecin 20-(2-bromo)-n-butyrate (6.048 g, 85%) as a light yellow solid.

Example 8

7-Hydroxymethyl camptothecin 20-(2-bromo)-n-butyrate

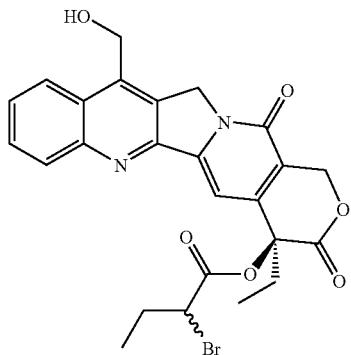

Camptothecin 20-(2-bromo)-n-butyrate (0.350 g) was suspended in a solution containing 20 mL methanol, 0.060 g $H_2SO_4$ and 0.100 g $FeSO_4$ heptahydrate that was dissolved in 0.250 g water. The solution was brought to reflux and hydrogen peroxide (1.0 mL) was added dropwise over the course of 1 hr. The reaction mixture was then cooled to rt and 5 mL water containing 0.050 g KOH was added. The solution was filtered and the solid recrystallized from methanol to provide 0.280 g (75%) 7-hydroxymethyl camptothecin 20-(2-bromo)-n-butyrate as a yellow solid.

Example 9

Method of Making HAR-7, Glycosylated 7-hydroxymethyl Camptothecin

As provided in FIG. 1, this method utilizes a dihydroxylated camptothecin compound that is rather insoluble in organic solvents. Because the dihydroxylated camptothecin is insoluble, the subsequent synthetic modification requires the use of an activated glycal, which is difficult to make and exists as four isomers (two pairs of regional isomers). The intermediate di-acetyl glycal as well as HAR-7 exists as diastereomers, which the Applicant was not able to separate by recrystallization or chromatographic methods (resulting in a single peak when by HPLC). Overall yield of the method was about 30%.

Method for the Preparation of the Hexanoate of Camptothecin at the 20 Hydroxyl

Figure 2:
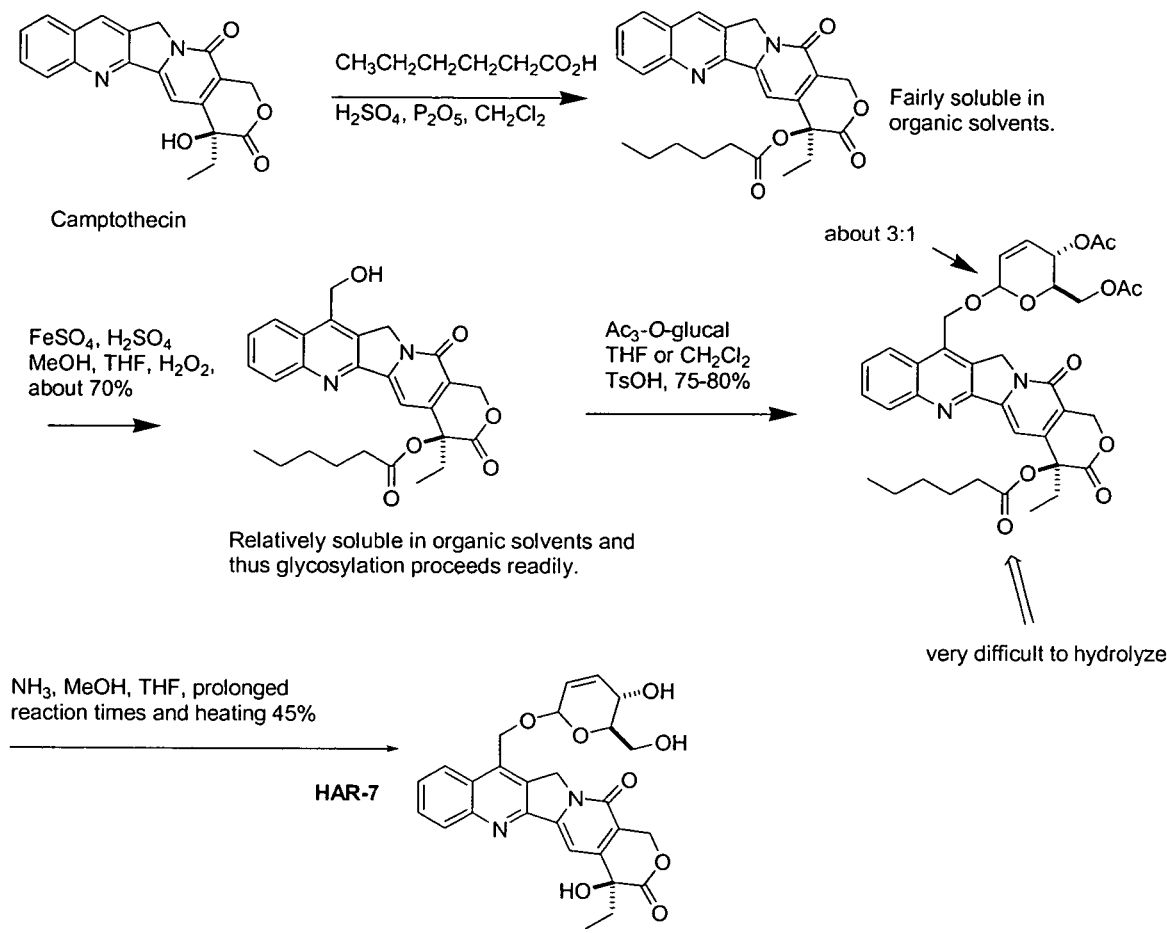
FIG. 2. Method for the preparation of the hexanoate of camptothecin at the 20 hydroxyl.

As provided in FIG. 2, this method utilizes a hexanoate protected camptothecin compound, which has desirable solubility properties. Producing the hexanote protected camptothecin in larger quantities using previous described procedures was inconsistent often resulting in low yields. A new method for the preparation of esters of sterically hindered alcohols using an organic acid (in this case hexanoic acid), sulfuric acid and phosphorus pentoxide provided the desired ester in yields above 90%. The product of the next step, 7-hydroxymethyl camptothecin 20-hexanoate, is reasonably soluble in organic solvents, thus the next synthetic transformation can be accomplished without the need to use activated glycals. However, the Applicant was unable to obtain separation of the diastereomers (i.e., alpha-isomer from the beta-isomer). Additionally, the hexanoate was difficult to hydrolyze under conditions that the camptothecin ring system was stable to (e.g., ammonia with gentle heating under pressure). Thus, attaching an ester at the 20 position solved one problem (i.e., the poor organic solubility of the 7-hydroxymethyl camptothecin) but introduced another, the removal of the new ester.

Method for Making HAR-7 Using Alpha-Bromobutyric Acid

Figure 3:
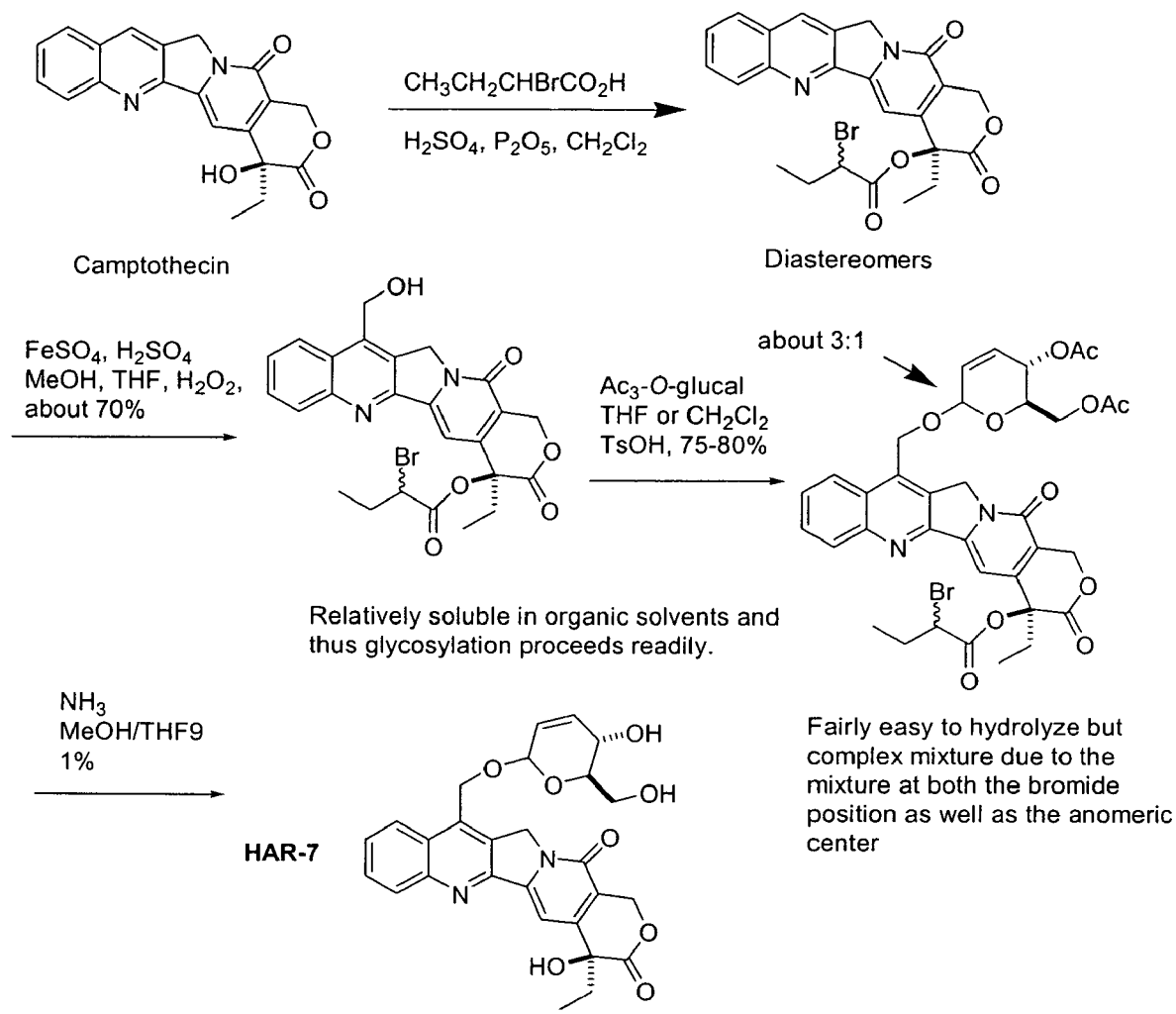
FIG. 3. Method for making HAR-7 using alpha-bromo butyric acid.

In order to expedite the hydrolysis of the ester at C-20, instead of preparing the 20-hexanoate the 2-bromobutyryl camptothecin derivative was made. As provided in FIG. 3, this method utilizes an alpha-bromo butyrate protected camptothecin compound, which has desirable solubility properties. Additionally, the alpha-bromo butyrate is removable under mild conditions using ammonia in methanol. However, the 2-bromobutyrate camptothecin derivative is a little more difficult to prepare, and the yield is a little lover due to incomplete esterification. The presence of an asymmetric alpha carbon produces a composition comprising additional diastereomers. The NMR spectra were more complex, and isolation of the diastereomers of the glycosylated analog could not be readily accomplished by recrystallization or using HPLC.

Method for Making HAR-7 Using 4-bromobutyric Acid

Figure 5:
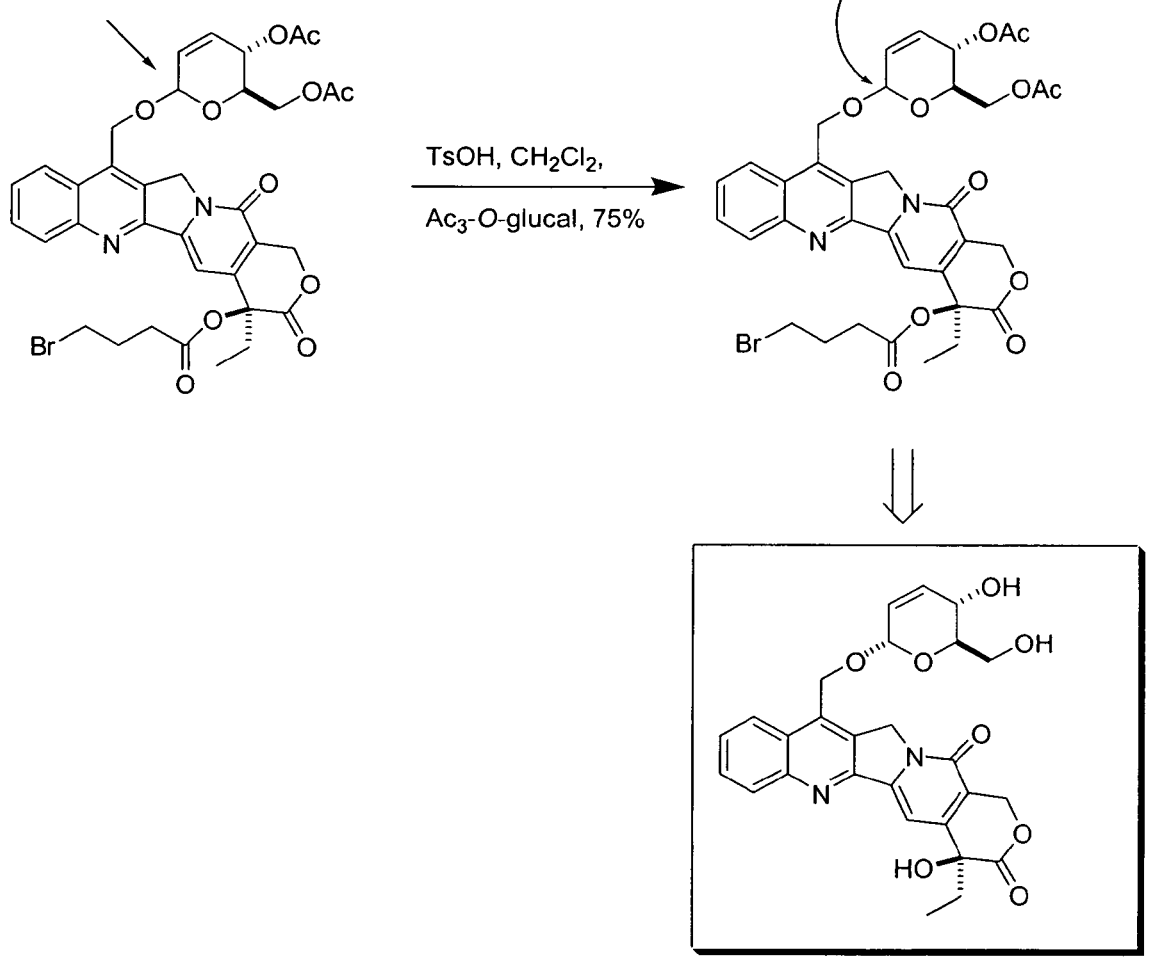
FIG. 5. Recycling Beta-rich isomer from recrystallization of the mother liquor.

The Applicant had difficulty in obtaining a composition comprising a single diastereomer of the alpha-isomer of the glycosylated camptothecin in pure from intermediates that contained protecting groups readily removable under mild conditions. This problem was solved by preparing 20-[4-bromobutyryl]camptothecin using 4-bromobutyric acid in the first acylating step. This compound is now routinely obtained in over 90% yield on a 25 gram scale. As provided in FIG. 4, this method utilizes a 4-bromobutyrate protected camptothecin compound, which has desirable solubility properties. In the next step, the formation of the 7-hydroxylmethyl group proceeds smoothly when dichloromethane is used as a co-solvent with methanol. Glycosylation proceeds with a little more difficulty than in the hexanoate case, due to a difference in solubility of the bromobutyrate derivative. However, the alpha-isomer from the glycosylation step can be isolated in pure form by recrystallization in methanol (about 50% recovery). One last advantage of this method is that after isolating the pure glycosylated alpha-isomer, the beta-rich composition can be recycled by exposing the composition to the original glycosylation conditions to ultimately obtain another composition containing a ratio of alpha-isomer to beta-isomer glycosylated product (See FIG. 5).

Figure 6:
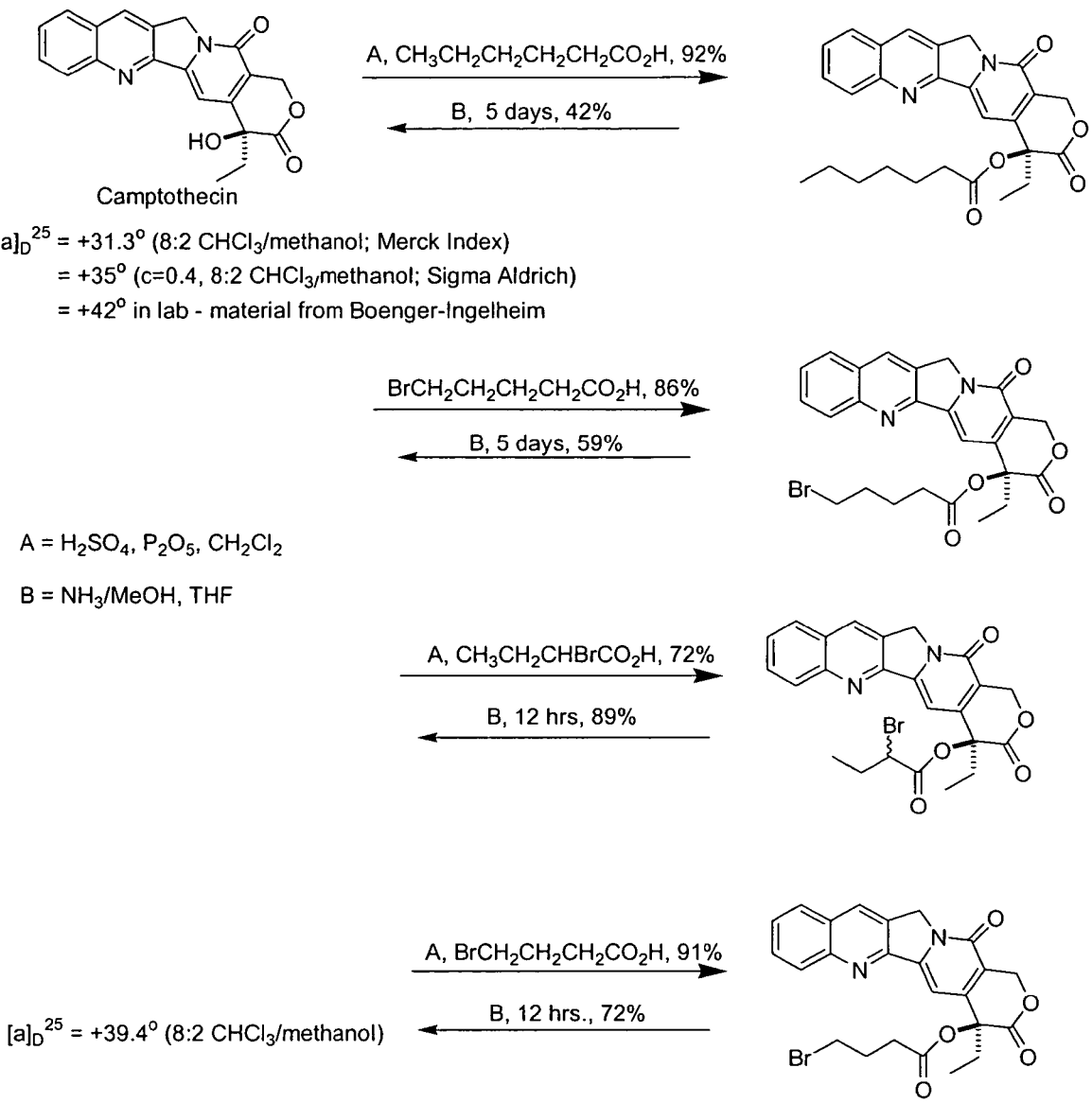
FIG. 6. Esterification/De-esterficiation of the C-20 Hydroxyl of Camptothecin.

Hydrolysis of the 4-bromobutyrate using ammonia, occurs quite readily. Although the Applicant does not intent the invention to be limited to any particular mechanism, it is believed that ammonia displaces the bromide, and the resultant primary amine, tethered to the ester, undergoes an intramolecular amide formation to expel 2-pyrrolidinone as a leaving group. The use of the 5-bromopentanoic acid resulted in a surprisingly sluggish deprotection compared to the 4-bromobutyrate derivative which provided the best results—efficient esterification and deprotection. The preparation and removal of the three esters, the hexanoate, 2-bromobutyrate and 4-bromobutyrate, along with 5-bromopentanoic acid, was studied in order to determine whether there is any loss in stereochemical purity at C-20 during the esterification procedure (See FIG. 6). Camptothecin has several different optical rotations reported, and the material that we purchased had a rotation of 41° after recrystallization. The camptothecin obtained after esterification/de-esterification under typical conditions for the 4-bromobutyrate has an optical rotation of +39.4°, (i.e., which we believe indicates little if no loss in the stereochemical integrity at C-20).

Figure 7:
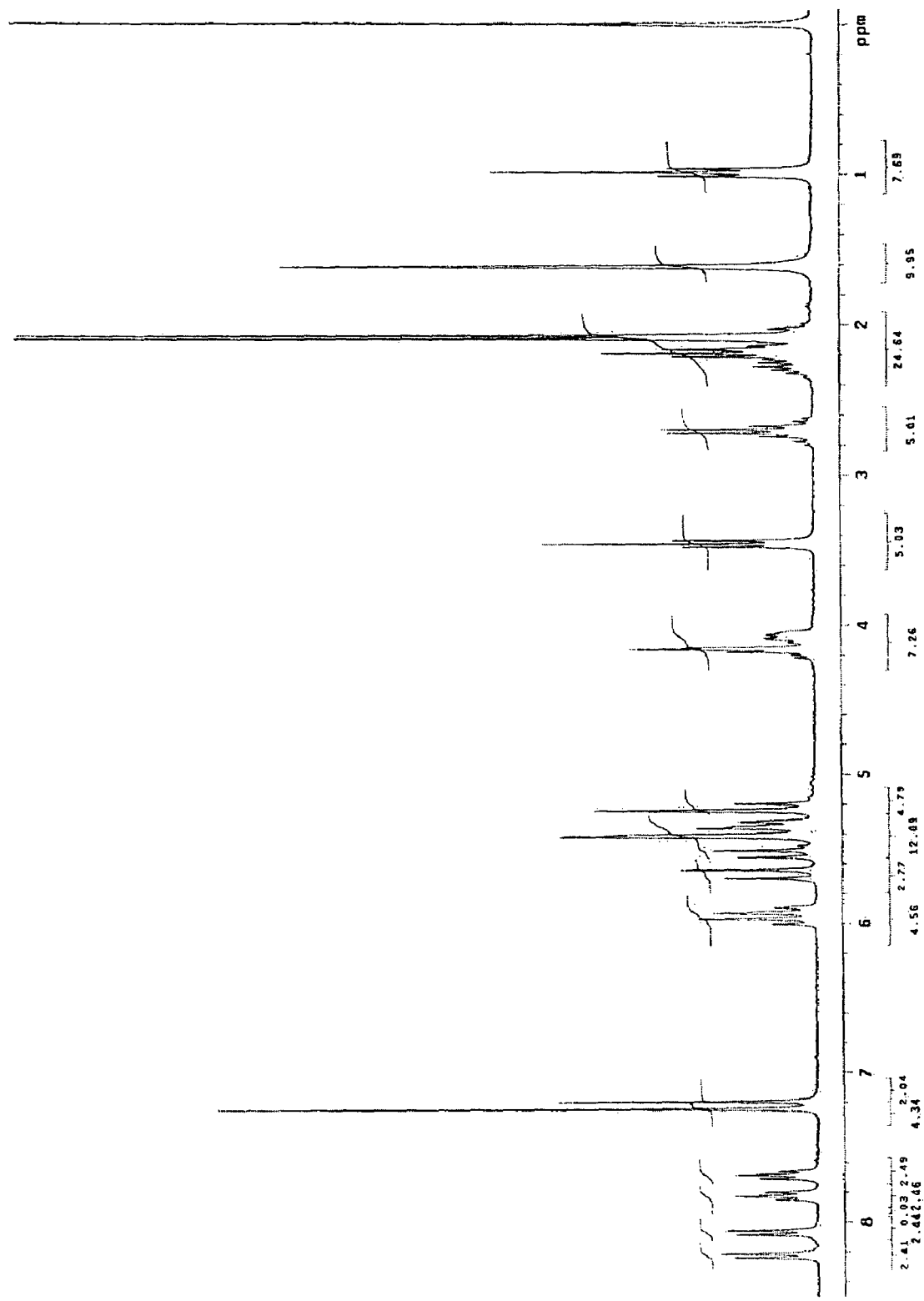
FIG. 7. $^1$H-NMR (300 MHz, CDCl$_3$) of the alpha-linked isomer of 7-[4'S,5'R-4',6'-di-O-acetyl-2',3'dideoxy-D-erythro-hex-2'-enopyranosyl]-oxymethyl camptothecin 20-(4-bromo)-n-butyrate.
Figure 8:
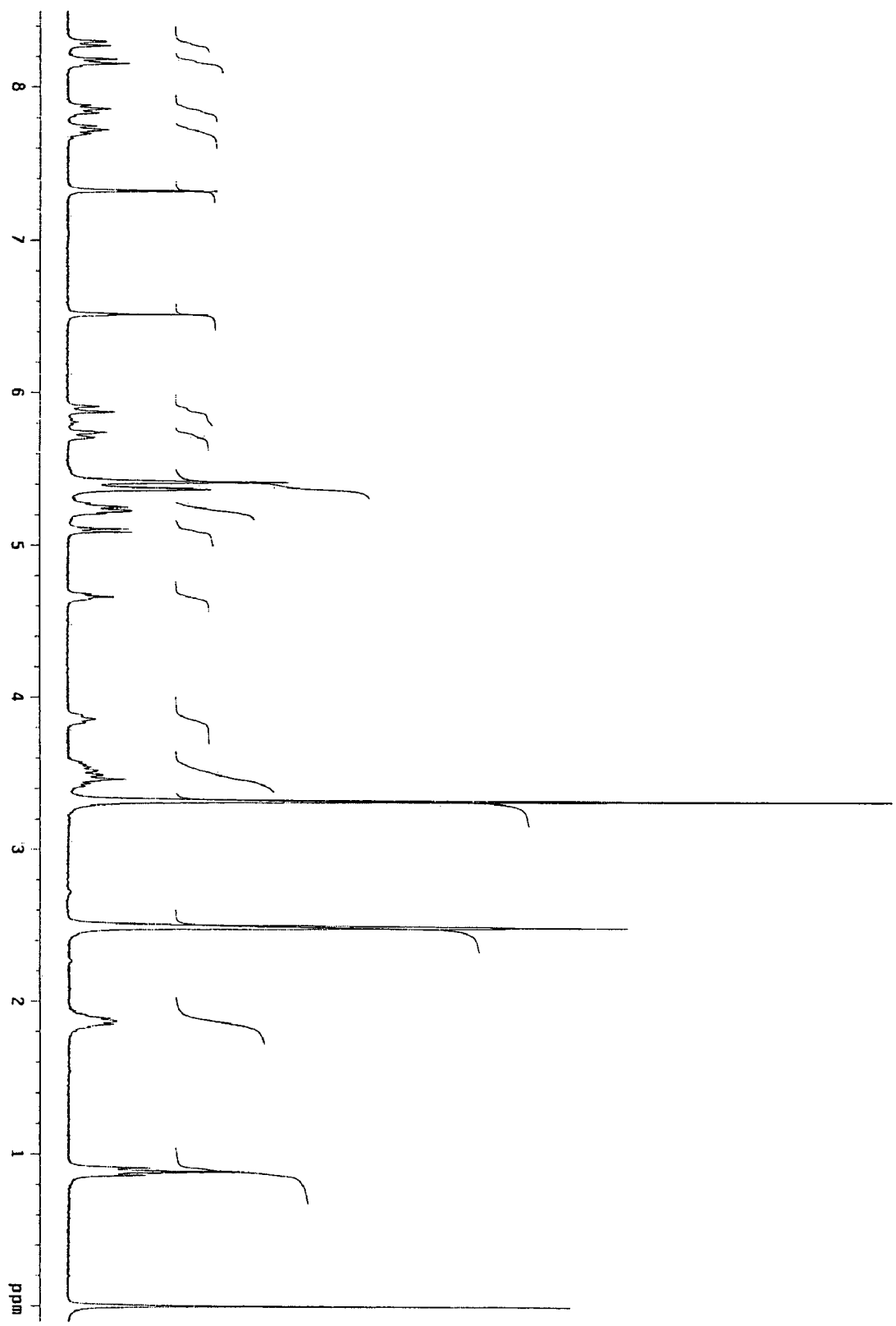
FIG. 8. $^1$H-NMR of (300 MHz, d$_6$-DMSO) of the alpha-linked isomer of HAR-7.
Figure 9:
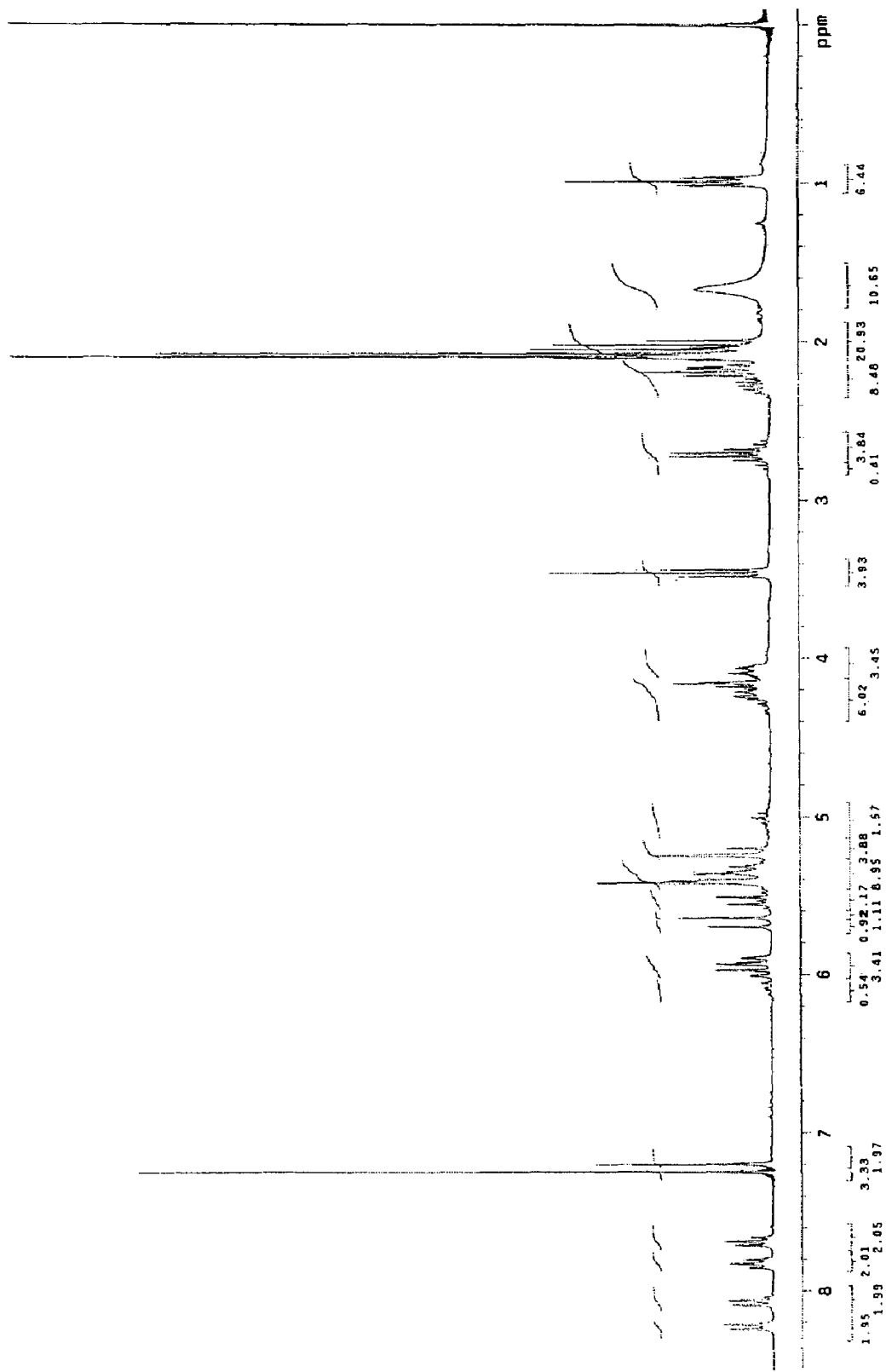
FIG. 9. $^1$H-NMR (300 MHz, CDCl$_3$) of an approximately 3 to 1 mixture of alpha-linked and beta linked isomer of 7-[4'S,5'R-4',6'-di-O-acetyl-2',3'-dideoxy-D-erythro-hex-2'-enopyranosyl]-oxymethyl camptothecin 20-(4-bromo)-n-butyrate.
Figure 10:
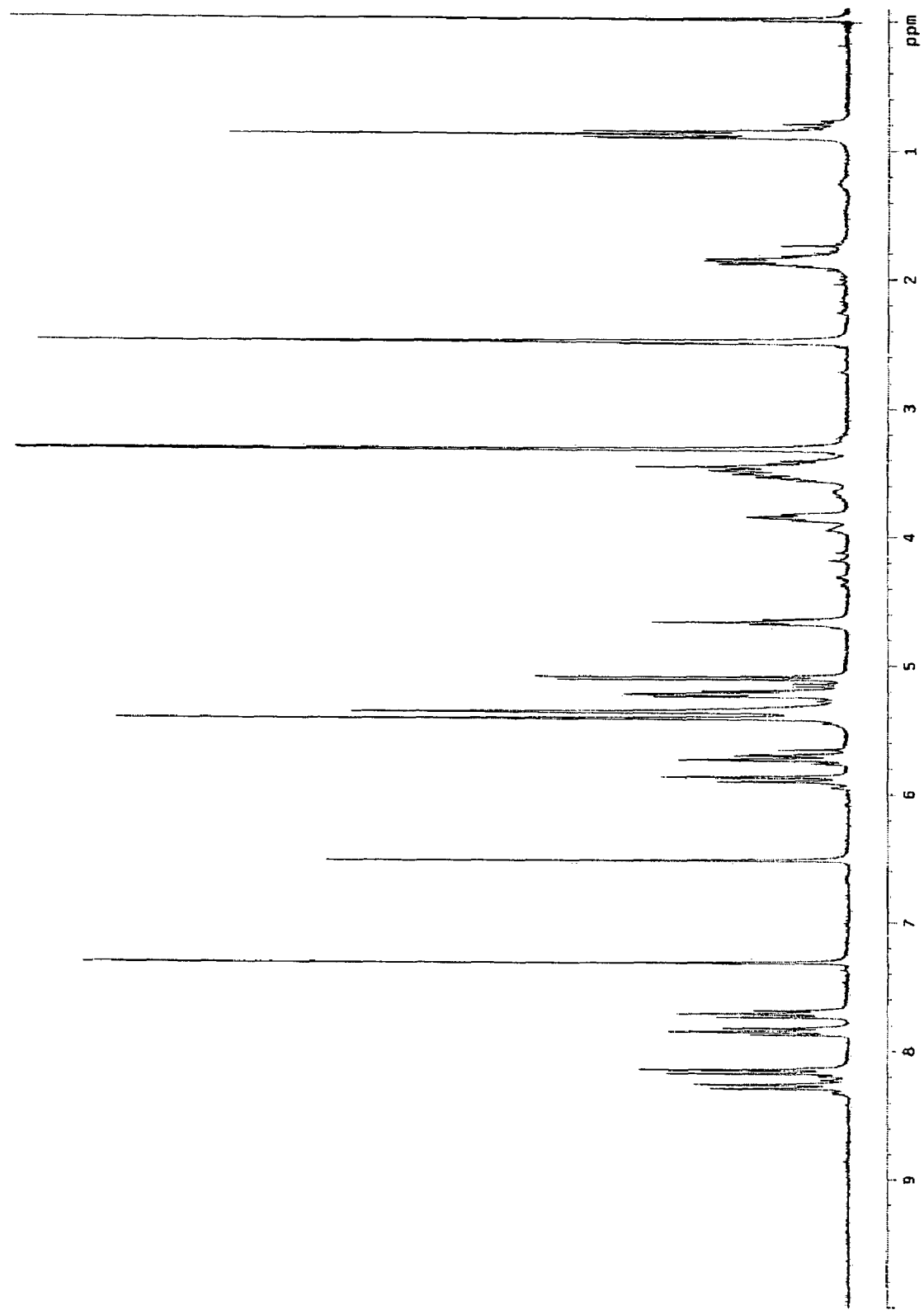
FIG. 10. $^1$H-NMR of (300 MHz, d$_6$-DMSO) of an approximately 3 to 1 mixture of alpha-linked and beta-linked isomer of HAR-7.
Figure 11:
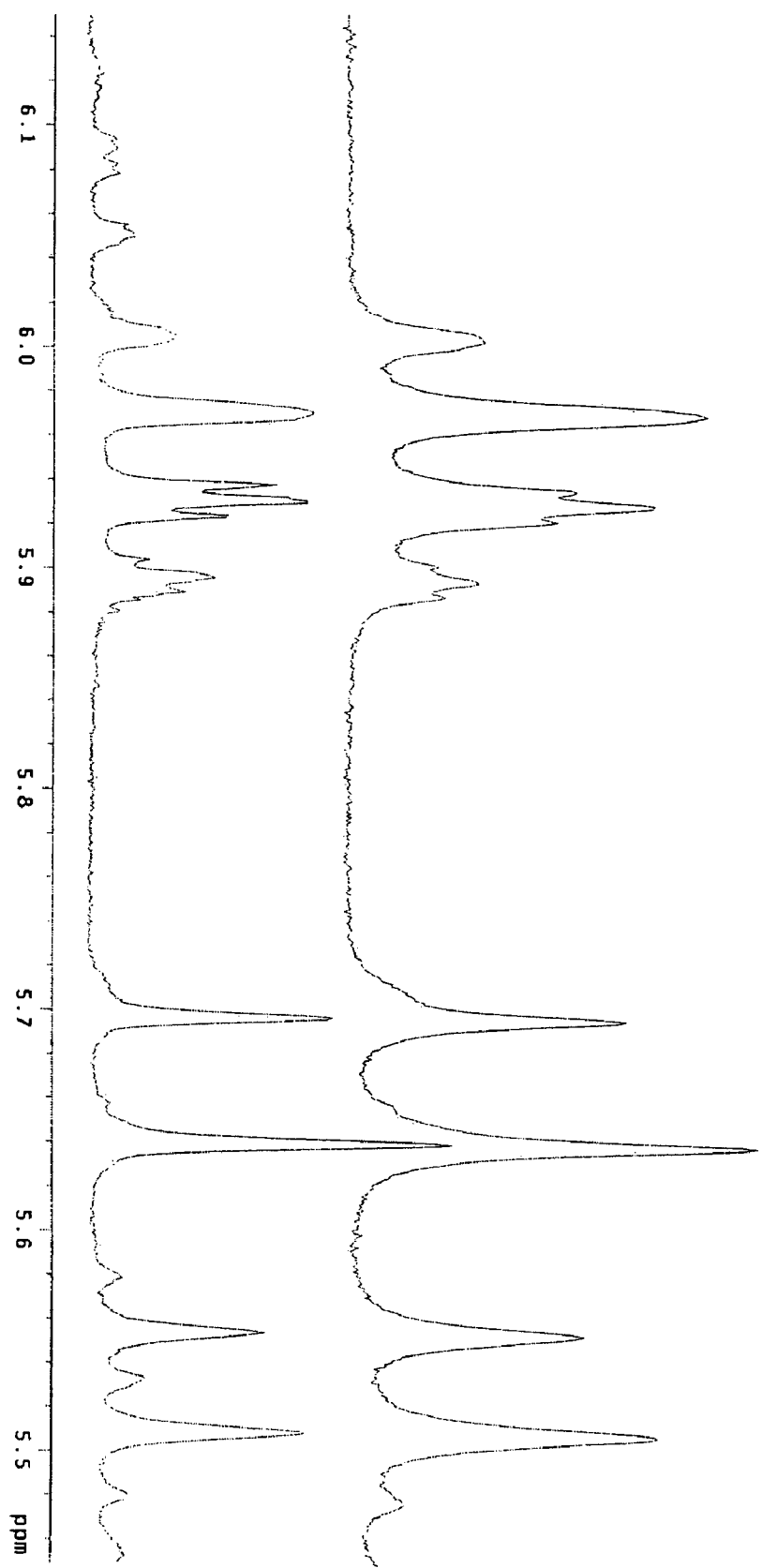
FIG. 11. Expanded regions of the 3 to 1 mixture of the alpha linked and beta linked isomer of 7-[4'S,5'R-4',6'-di-O-acetyl-2',3'-dideoxy-D-erythro-hex-2'-enopyranosyl]-oxymethyl camptothecin 20-(4-bromo)-n-butyrate before recrystallization in methanol (bottom spectrum) and after recrystallization (top spectrum).

What is claimed is:

1. A composition of 7-[4'S,5'R-4',6'-di-O-acetyl-2',3'-dideoxy-D-erythro-hex-2'-enopyranosyl]-oxymethyl camptothecin 20-(4-bromo)-n-butyrate having an $^1$H-NMR spectra as set out in FIG. 7.

2. The composition of claim 1, wherein said composition has an $^1$H-NMR with peaks consisting essentially of those provided in FIG. 7.

* * * * *